(12) United States Patent
Burton et al.

(10) Patent No.: US 10,391,290 B2
(45) Date of Patent: Aug. 27, 2019

(54) MICRONEEDLE INJECTION APPARATUS COMPRISING A DUAL COVER

(71) Applicant: 3M INNOVATIVE PROPERTIES COMPANY, St. Paul, MN (US)

(72) Inventors: Scott A. Burton, Woodbury, MN (US); Chin-Yee Ng, Oakdale, MN (US); Richard R. Mathias, Brookline, MA (US); Thomas D. R. Ford, Wellesley, MA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/866,526

(22) Filed: Jan. 10, 2018

(65) Prior Publication Data

US 2018/0140816 A1    May 24, 2018

Related U.S. Application Data

(63) Continuation of application No. 14/892,265, filed as application No. PCT/US2014/039135 on May 22, 2014, now Pat. No. 9,895,520.
(Continued)

(51) Int. Cl.
*A61M 5/24*    (2006.01)
*A61M 5/32*    (2006.01)
*A61M 37/00*   (2006.01)

(52) U.S. Cl.
CPC .......... *A61M 37/0015* (2013.01); *A61M 5/24* (2013.01); *A61M 5/32* (2013.01); *A61M 5/322* (2013.01);
(Continued)

(58) Field of Classification Search
CPC .......... A61M 37/0015; A61M 37/0046; A61M 2037/0023; A61M 2037/003;
(Continued)

(56) References Cited

U.S. PATENT DOCUMENTS 3,134,380 A    5/1964  Armao
4,472,480 A    9/1984  Olson
(Continued)

FOREIGN PATENT DOCUMENTS

CN    202173684 U    3/2012
EP    2399643        12/2011
(Continued)

OTHER PUBLICATIONS

International Search Report for PCT International Application No. PCT/US2014/039135, dated Sep. 4, 2014, 6 pages.

*Primary Examiner* — Laura A Bouchelle
*Assistant Examiner* — Dung T Ulsh

(57) ABSTRACT

A microneedle injection apparatus comprising a dual cover. The apparatus can include a housing having a base and a cavity; a microneedle array comprising a first side comprising a plurality of microneedles; and a microneedle array holder configured to hold a microneedle array and located in the housing. The microneedle array holder can be movable between a retracted position, and an extended position. The apparatus can further include a cover configured to be positioned to cover the opening in the base of the housing. The cover can include (i) a first portion configured to cover at least a portion of the base of the housing adjacent the opening, and (ii) a second portion configured to be received in the cavity of the housing and further configured to cover the plurality of microneedles on the microneedle array when the microneedle array holder is in the retracted position.

20 Claims, 10 Drawing Sheets

Related U.S. Application Data

(60) Provisional application No. 61/829,659, filed on May 31, 2013.

(52) U.S. Cl.
CPC ... *A61M 5/3202* (2013.01); *A61M 2005/2414* (2013.01); *A61M 2037/003* (2013.01); *A61M 2037/0023* (2013.01); *A61M 2037/0061* (2013.01)

(58) Field of Classification Search
CPC .. A61M 2037/0061; A61M 2005/1585; A61M 5/32; A61M 5/3295; A61M 5/3298
See application file for complete search history.

(56) References Cited

U.S. PATENT DOCUMENTS

| | | | |
|---|---|---|---|
| 4,584,355 A | 4/1986 | Blizzard | |
| 4,585,836 A | 4/1986 | Homan | |
| 4,591,622 A | 5/1986 | Blizzard | |
| 4,655,767 A | 4/1987 | Woodard | |
| 4,693,776 A | 9/1987 | Krampe | |
| 4,751,087 A | 6/1988 | Wick | |
| 4,834,979 A | 5/1989 | Gale | |
| 5,223,261 A | 6/1993 | Nelson | |
| 5,380,760 A | 1/1995 | Wendel | |
| 5,656,286 A | 8/1997 | Miranda | |
| 5,688,523 A | 11/1997 | Garbe | |
| 5,885,255 A | 3/1999 | Jaeger, Jr. | |
| 6,004,578 A | 12/1999 | Lee | |
| 6,024,976 A | 2/2000 | Miranda | |
| 6,091,975 A | 7/2000 | Daddona | |
| 6,149,935 A | 11/2000 | Chiang | |
| 6,312,612 B1 | 11/2001 | Sherman | |
| 6,365,178 B1 | 4/2002 | Venkateshwaran | |
| 6,379,324 B1 | 4/2002 | Gartstein | |
| 6,558,361 B1 | 5/2003 | Yeshurun | |
| 7,097,631 B2 | 8/2006 | Trautman | |
| 7,648,484 B2 | 1/2010 | Yeshurun | |
| D681,195 S | 4/2013 | Skulley | |
| 9,498,611 B2 | 11/2016 | Tokumoto | |
| 2002/0087182 A1 | 7/2002 | Trautman | |
| 2003/0054025 A1 | 3/2003 | Cantor | |
| 2004/0049150 A1 | 3/2004 | Dalton | |
| 2005/0261631 A1 | 11/2005 | Clarke | |
| 2008/0195035 A1 | 8/2008 | Frederickson et al. | |
| 2010/0121271 A1* | 5/2010 | Perriere | A61M 5/14248 604/110 |
| 2011/0172601 A1 | 7/2011 | Beebe | |
| 2011/0172638 A1 | 7/2011 | Moga | |
| 2011/0213335 A1 | 9/2011 | Burton | |
| 2011/0276027 A1 | 11/2011 | Trautman | |
| 2012/0109066 A1 | 5/2012 | Chase | |
| 2012/0123387 A1* | 5/2012 | Gonzalez | A61M 37/0015 604/506 |
| 2012/0143119 A1 | 6/2012 | Deasey | |
| 2015/0352295 A1 | 12/2015 | Burton | |

FOREIGN PATENT DOCUMENTS

| | | |
|---|---|---|
| WO | WO 1999-30759 | 6/1999 |
| WO | WO 2002-05889 | 1/2002 |
| WO | WO 2002-30300 | 4/2002 |
| WO | WO 2004-009172 | 1/2004 |
| WO | WO 2005-018705 | 3/2005 |
| WO | WO 2010-059605 | 5/2005 |
| WO | WO 2006-062974 | 6/2006 |
| WO | WO 2007-002521 | 1/2007 |
| WO | WO 2007-002522 | 1/2007 |
| WO | WO 2007-036676 | 4/2007 |
| WO | WO 2007-075806 | 7/2007 |
| WO | WO 2007-112309 | 10/2007 |
| WO | WO 2008-101892 | 8/2008 |
| WO | WO 2008-157592 | 12/2008 |
| WO | WO 2009-031144 | 3/2009 |
| WO | WO 2010-010974 | 1/2010 |
| WO | WO 2010-117602 | 10/2010 |
| WO | WO 2010-126174 | 11/2010 |
| WO | WO 2011-014514 | 2/2011 |
| WO | WO 2011-075105 | 6/2011 |
| WO | WO 2011-075569 | 6/2011 |
| WO | WO 2012-074576 | 6/2012 |
| WO | WO 2012-088154 | 6/2012 |
| WO | WO 2012-089627 | 7/2012 |
| WO | WO 2012-098503 | 7/2012 |
| WO | WO 2012-122162 | 9/2012 |
| WO | WO 2013-015136 | 1/2013 |
| WO | WO 2013-036602 | 3/2013 |
| WO | WO 2014-193725 | 12/2014 |
| WO | WO 2014-193729 | 12/2014 |

* cited by examiner

MICRONEEDLE INJECTION APPARATUS COMPRISING A DUAL COVER

CROSS REFERENCE TO RELATED APPLICATIONS

This application is continuation of U.S. patent application Ser. No. 14/892,265, filed Nov. 19, 2015, which is a national stage filing under 35 U.S.C. 371 of PCT/US2014/039135, filed May 22, 2014, which claims the benefit of U.S. Provisional Application No. 61/829,659, filed May 31, 2013, the disclosures of which are incorporated by reference in their entirety herein.

FIELD

The present disclosure generally relates to microneedle injection devices for applying microneedles to skin and/or delivering an active agent to skin.

BACKGROUND

Active agents (or drugs) are conventionally administered either orally or by injection. Unfortunately, many agents can be ineffective or have radically reduced efficacy when orally administered since they either are not absorbed or are adversely affected before entering the bloodstream and thus do not possess the desired activity. Further, orally administered agents may not take effect as quickly as injected agents. On the other hand, the direct injection of the agent into the bloodstream, while assuring no modification of the agent during administration, is a difficult, inconvenient, painful and uncomfortable procedure which sometimes results in poor patient compliance.

Transdermal delivery can provide a method of administering active agents that would otherwise need to be delivered via hypodermic injection or intravenous infusion. In addition, transdermal delivery, when compared to oral delivery, avoids the harsh environment of the digestive tract, bypasses gastrointestinal drug metabolism, reduces first-pass effects, and avoids the possible deactivation by digestive and liver enzymes.

In some cases, however, the number of molecules that can be effectively delivered using transdermal delivery can be limited by the barrier properties of skin. The main barrier to the transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which make up the majority of epidermal cells, that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Microneedle or micro-pin arrays, also sometimes referred to as microstructured transdermal systems (MTSs), provide intradermal delivery of active agents, which otherwise would not penetrate the stratum corneum. The sharp microneedle tip is designed to be able to penetrate the stratum corneum layer of the skin, but short enough not to puncture nerve endings, thus reducing or eliminating pain upon insertion. However, the penetration of microneedles to precise levels within the skin tissue and with good reproducibility is often a challenging task. Therefore, unlike the application of traditional patch-based delivery systems, some existing MTSs require the assistance of external energy to ensure efficient and reproducible penetration of microneedles into biological tissue at desired depths. This assistance can be achieved by utilizing an apparatus device, which can either be used after positioning the microneedle array on the skin surface, or the apparatus device can be integrated with an array of microneedles and, upon activation, can deliver the microneedle array into the skin. The microneedles help to create microchannels in the skin, which in some embodiments, can facilitate delivering an active ingredient. In some constructions, active component (s) may be coated on the microneedle array and delivered directly through the skin when the stratum corneum is punctured by the microneedles. One advantage of MTS systems over other skin treatment methods is a reduced-pain mode of delivery.

SUMMARY

Some embodiments of the present disclosure provide a microneedle injection apparatus that can include a housing having a base and a cavity that extends through the base to define an opening in the base, wherein the base of the housing is configured to be positioned toward a skin surface. The apparatus can further include a microneedle array comprising a first side comprising a plurality of microneedles. The apparatus can further include a microneedle array holder configured to hold a microneedle array and located in the housing. The microneedle array holder can be movable with respect to the opening in the base of the housing between (i) a retracted position in which the microneedle array is recessed within the housing such that the microneedle array does not contact the skin surface when the apparatus is positioned on the skin surface and the microneedle array is coupled to the microneedle array holder, and (ii) an extended position in which at least a portion of the microneedle array is positioned to contact the skin surface via the opening when the apparatus is positioned on the skin surface and the microneedle array is coupled to the microneedle array holder. The apparatus can further include a cover configured to be positioned to cover the opening in the base of the housing. The cover can include (i) a first portion configured to cover at least a portion of the base of the housing adjacent the opening, and (ii) a second portion configured to be received in the cavity of the housing and further configured to cover the plurality of microneedles on the microneedle array when the microneedle array holder is in the retracted position.

Other features and aspects of the present disclosure will become apparent by consideration of the detailed description and accompanying drawings.

DETAILED DESCRIPTION

Figure 1:
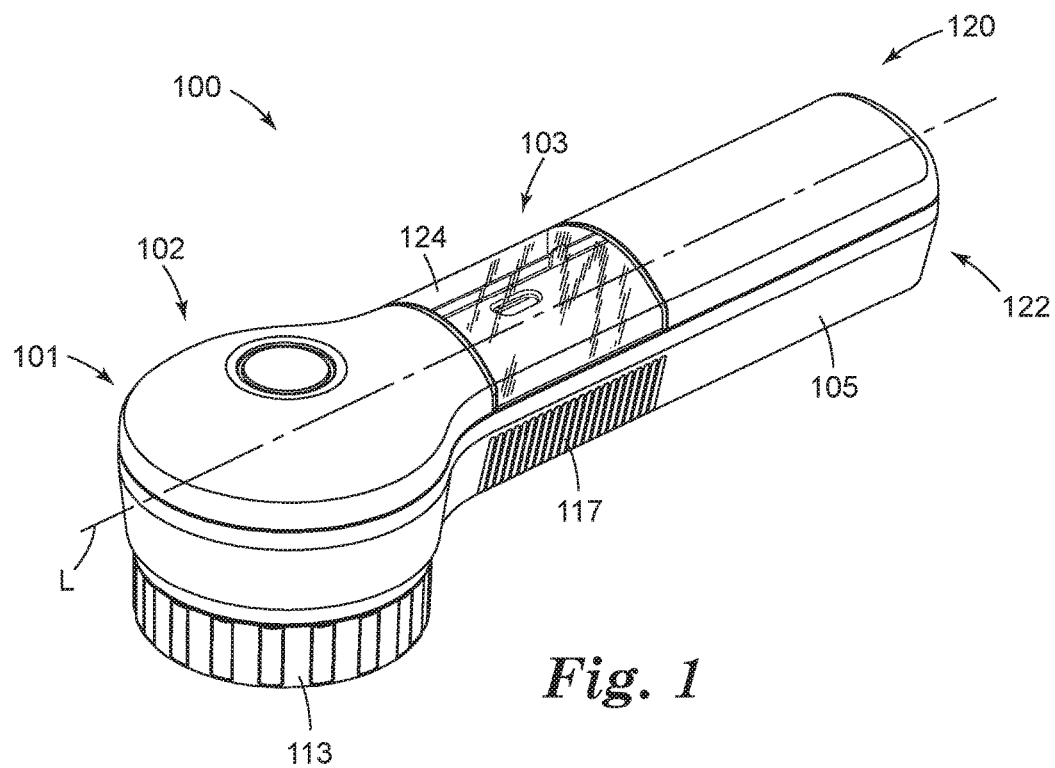
FIG. 1 is a front assembled top perspective view of a microneedle injection apparatus according to one embodiment of the present disclosure, the apparatus including a cover, and injection assembly, and an infusion assembly.
Figure 2:
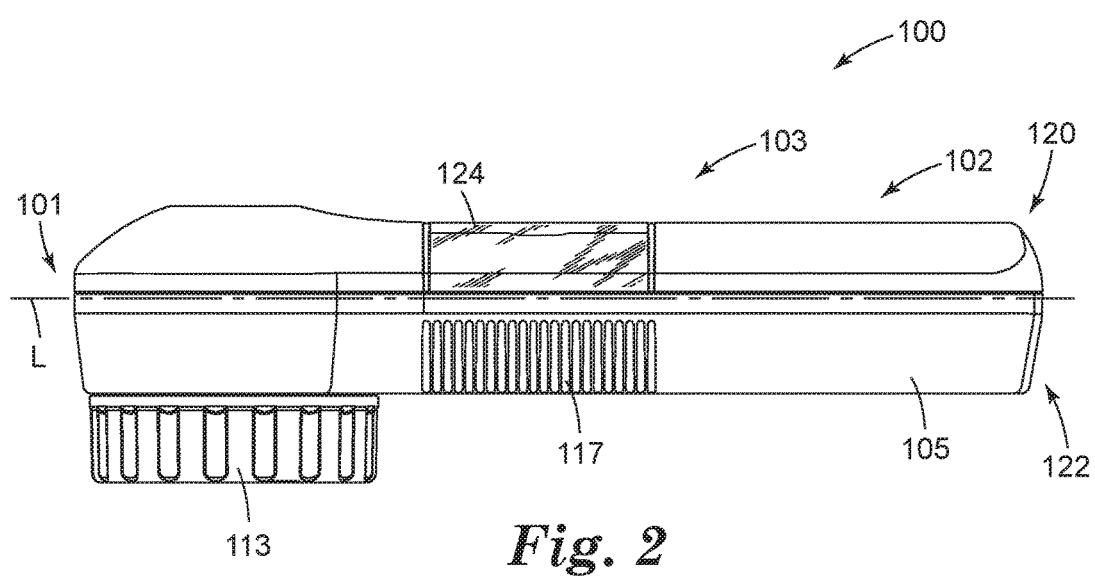
FIG. 2 is a side view of the apparatus of FIG. 1.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "supported," and "coupled," and variations thereof, are used broadly and encompass both direct and indirect mountings, supports, and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to microneedle injection apparatuses and methods of using same. Apparatuses of the present disclosure can include an array of microneedles that can be applied to skin (or a biological membrane) to treat the skin (i.e., create small holes or perforations or micropores in the skin) and can also deliver an active agent to the skin. Apparatuses of the present disclosure further include a 'dual cover' that can include (i) a first portion configured to cover a least a portion of a base that will be coupled (e.g., via a skin-contact adhesive) to a patient's skin and (ii) a second portion configured to be received in a cavity of a housing of the apparatus and further configured to cover and protect the microneedles prior to use, i.e., when the microneedles are in a retracted position. The second portion of the cover can provide at least a portion of a sterile chamber configured to house the microneedles prior to use, which can maintain the sterility of the microneedles as well as any fluid path that includes, or is in fluid communication with, the microneedles (e.g., in embodiments employing an on-board infusion device and hollow microneedles).

The phrase "hollow microneedle" refers to a specific microscopic structure that includes a lumen formed therein. The hollow microneedles of the present disclosure are designed for piercing the stratum corneum to facilitate the delivery of active agents through the skin, e.g., via each lumen. By way of example, microneedles can include needle or needle-like structures, as well as other structures capable of piercing the stratum corneum and delivering the active agent. Additional details about microneedles that can be employed with the apparatuses of the present disclosure are described in greater detail below.

Some embodiments of apparatuses of the present disclosure can be configured to appropriately time and stage a sequence of events following actuation, such that, e.g., the microneedles are in place, penetrating the skin, before the active agent begins to be dispensed or released from the on-board infusion device. For example, in some embodiments, apparatuses of the present disclosure can include an injection assembly or device that includes a microneedle array holder, and an infusion assembly or device that includes a cartridge that defines a reservoir configured to contain an active agent. An actuator can be actuated to cause the injection device to inject microneedles into the skin and to initiate infusion of the active agent from the injection device through the injection device into the skin. In some embodiments, at least a portion of the infusion device can hold the injection device in a retracted position until the actuator causes the infusion device to move and release the injection device. By way of example only, and as described in greater detail below, the actuator can be moved from a first position to a second position, which releases a shuttle of the infusion device that holds and carries the cartridge, which in turn releases at least a portion of the injection device (e.g., the microneedle array holder). In some embodiments, the shuttle can continue moving after the injection device penetrates the skin to move the cartridge to an infusing position where the reservoir of the cartridge is in fluid communication with a fluid path (e.g., including hollow microneedles penetrating the skin). The active agent can then be forced out of the reservoir of the cartridge into the fluid path to deliver the active agent to the skin.

Apparatuses of the present disclosure may be useful when applied to the skin as a "pretreatment" step, that is, when applied to the skin to disrupt the stratum corneum layer of skin and then removed. The disrupted area of skin may then be useful for allowing enhanced delivery of a topical composition (e.g., a solution, a cream, a lotion, a gel, an ointment, or the like) or patch comprising an active agent that is applied to the disrupted area. Apparatuses of the present disclosure may also be useful when the microneedles are provided with a dried coating comprising an active agent that dissolves from the microneedles after they are inserted into the skin. As a result, apparatuses of the present disclosure may have utility for enhancing delivery of molecules to the skin, such as in dermatological treatments, vaccine delivery, or in enhancing immune response of vaccine adjuvants. Furthermore, in some embodiments, the active agent may be applied to the skin (e.g., in the form of a solution that is swabbed onto the skin surface, or as a cream, lotion, gel, ointment, or the like, that is rubbed into the skin surface) prior to applying the microneedles of the apparatuses of the present disclosure.

When a patch is applied to the treated or disrupted site, the patch can be provided in a variety of forms and can include a drug reservoir comprising an active agent for delivery to the treated site. Any transdermal patch suitable for the continuous transdermal delivery of a therapeutically effective amount of an appropriate medicament may be used. Suitable transdermal patches include gelled or liquid reservoirs, such as in U.S. Pat. No. 4,834,979 (Gale), so-called "reservoir" patches; patches containing matrix reservoirs attached to the skin by an adjacent adhesive layer, such as in U.S. Pat. No. 6,004,578 (Lee et al.), so-called "matrix" patches; and patches containing pressure-sensitive adhesive (PSA) reservoirs, such as in U.S. Pat. No. 6,365,178 (Venkateshwaran et al.), U.S. Pat. No. 6,024,976 (Miranda et al.), U.S. Pat. No. 4,751,087 (Wick) and U.S. Pat. No. 6,149,935 (Chiang et al.), so-called "drug-in-adhesive" patches, the disclosures of which are hereby incorporated by reference. In some embodiments, the drug reservoir can be provided in the form of a matrix layer containing drug, the matrix layer being adhered to a skin-contact adhesive of the patch. Such a matrix may be an adhesive layer. Alternatively, the matrix layer may be non-adhesive or weakly adhesive and rely upon the surrounding rim of skin-contact adhesive on an adhesive patch to secure the patch in place and keep the drug reservoir in contact with the skin surface.

In another embodiment, the drug reservoir can be provided in the form of solid particles embedded on the surface or within the skin-contact adhesive of the patch. In particular, these particles may be hydrophilic, so that contact with aqueous fluid exposed at the surface of the treated skin will cause them to dissolve or disintegrate, thus releasing drug into the skin.

In another embodiment, the drug reservoir can be provided within the skin-contact adhesive of the patch. The drug may be mixed with the skin-contact adhesive prior to forming the patch or it may be applied to the skin-contact adhesive of the patch in a separate process step. Examples of suitable methods for applying drug to an adhesive layer may be found in U.S. Patent Application Publication No. 2003/054025 (Cantor et al.) and U.S. Pat. No. 5,688,523 (Garbe et al.), the disclosures of which are hereby incorporated by reference.

The length of time between (i) treatment of the skin with microneedles to increase permeability and (ii) placement of the active agent in contact with the treated skin area may vary. In some embodiments, this length of time can be kept to a minimum in order to avoid any possibility of the skin barrier reforming through a healing process. The minimum length of time can be generally governed by the time it takes to remove the apparatuses of the present disclosure from the skin and apply the active agent, for example, by swabbing on a solution, rubbing in a cream or lotion, remove the liner of a patch and applying its adhesive over the treated site (e.g., if a patch is being employed), etc. This time may be less than about 1 minute, less than about 30 seconds, less than about 10 seconds, or less than about 5 seconds. There is no reason, however, that this time cannot be extended to many minutes or hours if so desired. It is generally known that the length of time that the skin will remain increasingly permeable after treatment depends on the type of treatment and whether the skin is occluded or not after treatment. In some instances, increased permeability can be maintained for up to several days as long as the treated site remains occluded and even in the absence of occlusion the skin may have increased permeability for up to several hours. Thus, if it presented some convenience or clinical benefit, one could treat the site and delay delivery of an active agent/ingredient by wearing some type of dressing over the treated site until such time as one desired to begin delivery of the active agent, at which time the active agent could be applied to the treated skin.

In discussing the apparatuses of the present disclosure, the term "downward," and variations thereof, is sometimes used to describe the direction in which microneedles are pressed into skin, and "upward" to describe the opposite direction. However, those of skill in the art will understand that the apparatuses can be used where the microneedles are pressed into skin at an angle to the direction of the earth's gravity, or even in a direction contrary to that of the earth's gravity, and these terms are only used for simplicity and clarity to describe relative directions.

FIGS. 1-11 illustrate a microneedle injection apparatus 100 according to one embodiment of the present disclosure. As shown, in some embodiments, the apparatus 100 can include an injection assembly (or device) 101 and an infusion assembly (or device) 103, which can be an on-board infusion device. Even though the illustrated embodiment includes both the injection assembly 101 and the infusion assembly 103, in some embodiments, the apparatus 100 can include only the injection assembly 101, and does not include an on-board infusion device such as the infusion assembly 103 that houses an active agent to be delivered to the skin via hollow microneedles.

The phrase "on-board infusion device" generally refers to an assembly or device capable of delivering an active agent to the microneedles of the injection assembly 101 for delivery to a patient's skin that forms a portion of, or is coupled to, and is operable with the injection assembly 101.

In some embodiments, the apparatus 100 can be referred to as a "controlled fluid release apparatus." In addition, the injection assembly 101 can also be referred to as an "applicator" or a "microneedle applicator;" and the infusion assembly 103 can also be referred to as a "fluid storage and delivery system or assembly."

The apparatus 100 can further include a housing 102; an actuator 104; a microneedle array holder 106 configured to hold and carry a microneedle array 107 comprising a plurality of microneedles 108; a cartridge 110 defining a reservoir 111 configured to contain an active agent; and a cover 113. As shown in FIGS. 1, 2, 4 and 5, in some embodiments, the housing 102 can include a ridged or texturized surface or portion 117 to facilitate manually grasping and/or manipulating the apparatus 100.

In some embodiments, the cartridge 110 can be installed by manufacturers, assemblers, or users. In addition, the cartridge 110 and the microneedle array 107 can be replaced, thereby permitting reuse of the apparatus 100. Replaceable cartridges may provide an advantage of being able to be cleaned, sterilized, filled, and refilled as compared to microneedle devices having fixed or dedicated cartridges that are integrally formed therewith.

Figure 3:
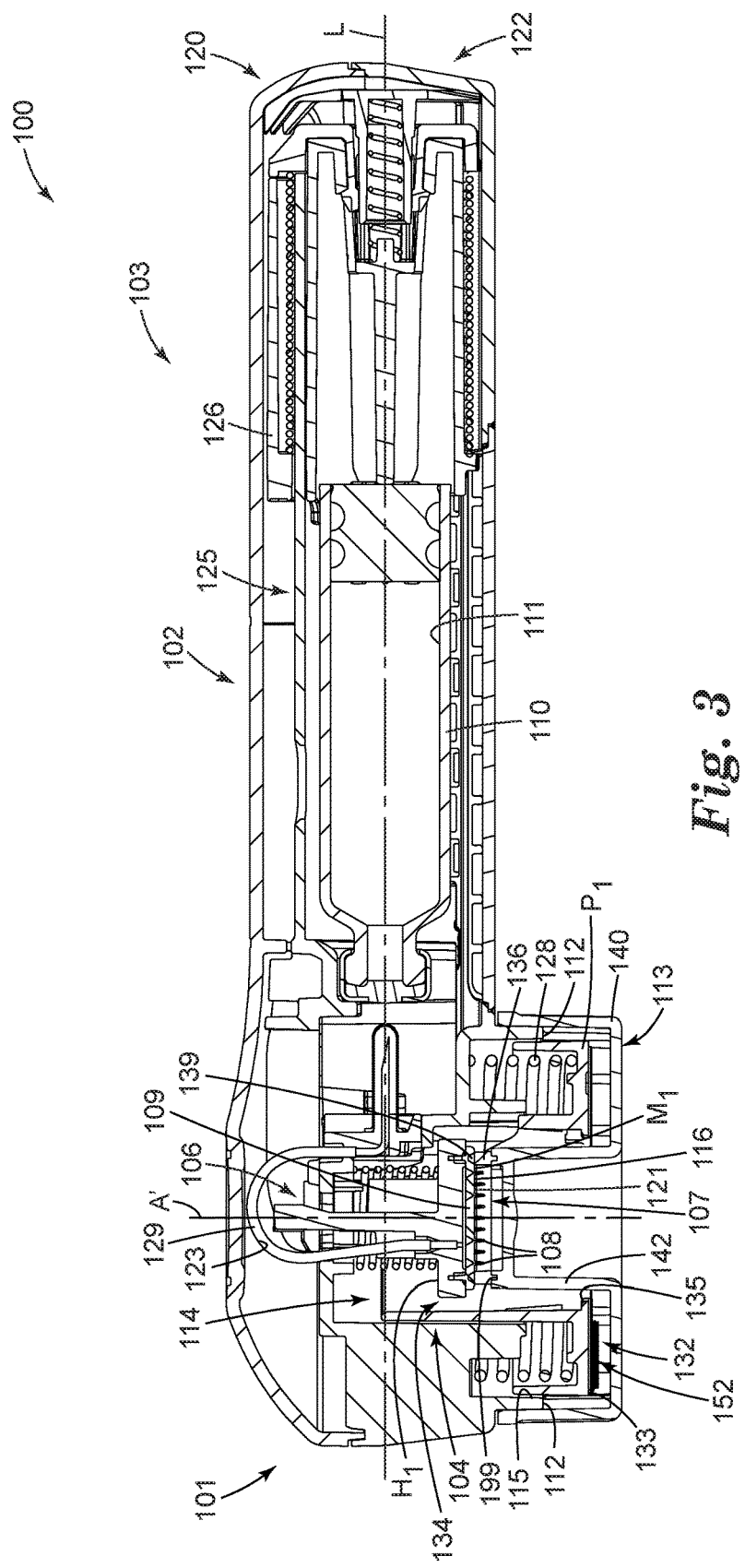
FIG. 3 is a side cross-sectional view of the apparatus of FIGS. 1 and 2.

As shown in FIG. 3, the injection assembly 101 can include the microneedle array holder 106 and a microneedle array 107 (i.e., when coupled to the microneedle array holder 106), and the infusion assembly 103 can include the cartridge 110. In some embodiments, the apparatus 100 can further include a fluid path 123 that is in fluid communication with or includes the microneedle array 107 (e.g., any surfaces or manifolds thereof, as well as the hollow microneedles 108), when the microneedle array 107 is coupled to the microneedle array holder 106. As a result, the fluid path 123 can deliver an active agent to and through the hollow microneedles 108. Such a fluid path 123 can provide fluid communication between the injection assembly 101 and the infusion assembly 103 and therefore, in some embodiments, can be described as forming a portion of either assembly, or as a connection between the assemblies.

In some embodiments, at least a portion of the fluid path 123 can be formed by a conduit or channel positioned to fluidly connect the cartridge 110 and the microneedles 108. In some embodiments, that conduit or channel can be provided by flexible tubing 129 (see FIGS. 3, 4 and 6). In some embodiments, one end of such tubing can be coupled to the microneedle array 107 and can travel with the microneedle array 107 (and microneedle array holder 106). Such flexible tubing 129 can allow a piercing element 175 that is in fluid communication with the fluid path 123 and is configured to pierce or puncture the cartridge 110 to remain in a fixed location within the housing 102. As such, the piercing element 175 need not travel with the microneedle array 107 and holder 106. Such tubing 129 can be formed of a variety of materials, including, but not limited to, polymeric materials, such as polypropylene, polyethylene, silicone, other suitable polymeric materials, or a combination thereof. However, in some embodiments, the piercing element 175 can be fixedly coupled to the holder 106, the apparatus 100 need not include the flexible tubing 129, and the piercing element 175 can be movable in the housing 102 with the microneedle array 107 and the holder 106.

The infusion assembly 103 can further include a shuttle 125 configured to hold and carry the cartridge 110 into fluid communication with the fluid path 123. The actuator 104 can be operable to actuate injection, and, in some embodiments, can further actuate movement of the shuttle 125 (and, accordingly, the cartridge 110) and infusion of the active agent into the fluid path 123 and out the hollow microneedles 108.

In some embodiments, the microneedles 108 can be configured to treat skin (i.e., create small holes or perforations or micropores in the skin) and/or deliver an active agent via skin, particularly, mammalian skin, and particularly, transdermally. Various microneedles that can be employed in apparatuses and methods of the present disclosure are described in greater detail below. In embodiments in which the microneedles 108 are hollow and configured to deliver an active agent, each hollow microneedle 108 can includes a lumen. While a "plurality of microneedles" 108 is described in the present disclosure, it should be understood that not all of the microneedles 108 in a given array 107 are required to penetrate the skin (or to be coated with an active agent in embodiments in which the microneedles 108 include a coating) in a given use.

The term "transdermally," and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across or through at least a portion of skin (but not necessarily all of the layers of skin), rather than merely being topically applied to an outer layer of the skin.

In some embodiments, the housing 102 can be self-contained and compactly constructed to provide a relatively low profile and small footprint for, among other factors, ease of use and patient comfort. The term "footprint" generally refers to the surface area occupied by an item (e.g., the apparatus 100), e.g., on a skin surface. The footprint of a given item can be thought of as the area taken up by an outline of the outermost dimensions of the item. In some embodiments, "low profile" can refer to an apparatus 100 that is generally wide in relation to its height. That is, a "low profile" device can be one that has a dimension that extends along the skin surface that is greater than a dimension which extends generally normal to (and away from) the skin surface. Said another way, "low profile" can refer to a device having a skin-parallel dimension that is greater than its skin-normal dimension.

As shown, the apparatus 100, and the housing 102, can be elongated along a longitudinal axis L (see, e.g., FIGS. 1 and 2) and can be configured to be oriented substantially parallel with respect to a skin surface when in use. Such a configuration can provide a low profile for the apparatus 100. A low profile can reduce the likelihood of the microneedles 108 becoming dislodged during penetration and/or infusion and can facilitate hands-free wear. While designing the apparatus 100 such that the longitudinal axis L will be oriented generally parallel to a patient's skin surface during use can provide a low-profile and compact design, other orientations can be employed.

In some embodiments, the housing 102 can be formed of more than one portion. In some embodiments, the housing 102 can include a first (or upper) portion 120 adapted to be coupled (e.g., removably or permanently) to a second (or lower) portion 122, such that the first portion 120 can function as a cover for the second portion 122. At least a portion of the housing 102 (e.g., the first portion 120) can include one or more light-transmissive windows 124, which in some embodiments, can allow a user to observe the progress of at least a portion of the infusion process. For example, in some embodiments, the infusion assembly 103 can include one or more indicators 126 for indicating the progress of infusion, and such indicators 126 can be visible via the window 124. The window(s) 124 need not be entirely transparent but at least partially transmissive to wavelengths in the visible spectrum (i.e., about 400 nm to about 700 nm) to allow for visual detection of the indicator(s) 126 via the window(s) 124.

The second portion 122 of the housing 102 can be configured to hold and retain the injection assembly 101 and the infusion assembly 103. Each of the first portion 120 and the second portion 122 of the housing can include one or more retaining walls 105. The first portion 120 and the second portion 122 of the housing 102 can be configured to be coupled together by a variety of coupling means, including, but not limited to, press-fit engagement (also sometimes referred to as "friction-fit engagement" or "interference-fit engagement"), snap-fit engagement, magnets, hook-and-loop fasteners, adhesives, cohesives, clamps, stitches, staples, screws, nails, rivets, brads, crimps, detents, welding (e.g., sonic (e.g., ultrasonic) welding), any thermal bonding technique (e.g., heat and/or pressure applied to one or both of the components to be coupled), other suitable coupling means, or combinations thereof. By way of example only, in the embodiment of FIGS. 1-11, the first portion 120 and the second portion 122 are configured to be ultrasonically welded together. In addition, the housing 102 is shown as being split along its length into the first portion 120 and the second portion 122; however, other configurations are possible that also facilitate assembly and/or use of the apparatus 100.

Figure 6:
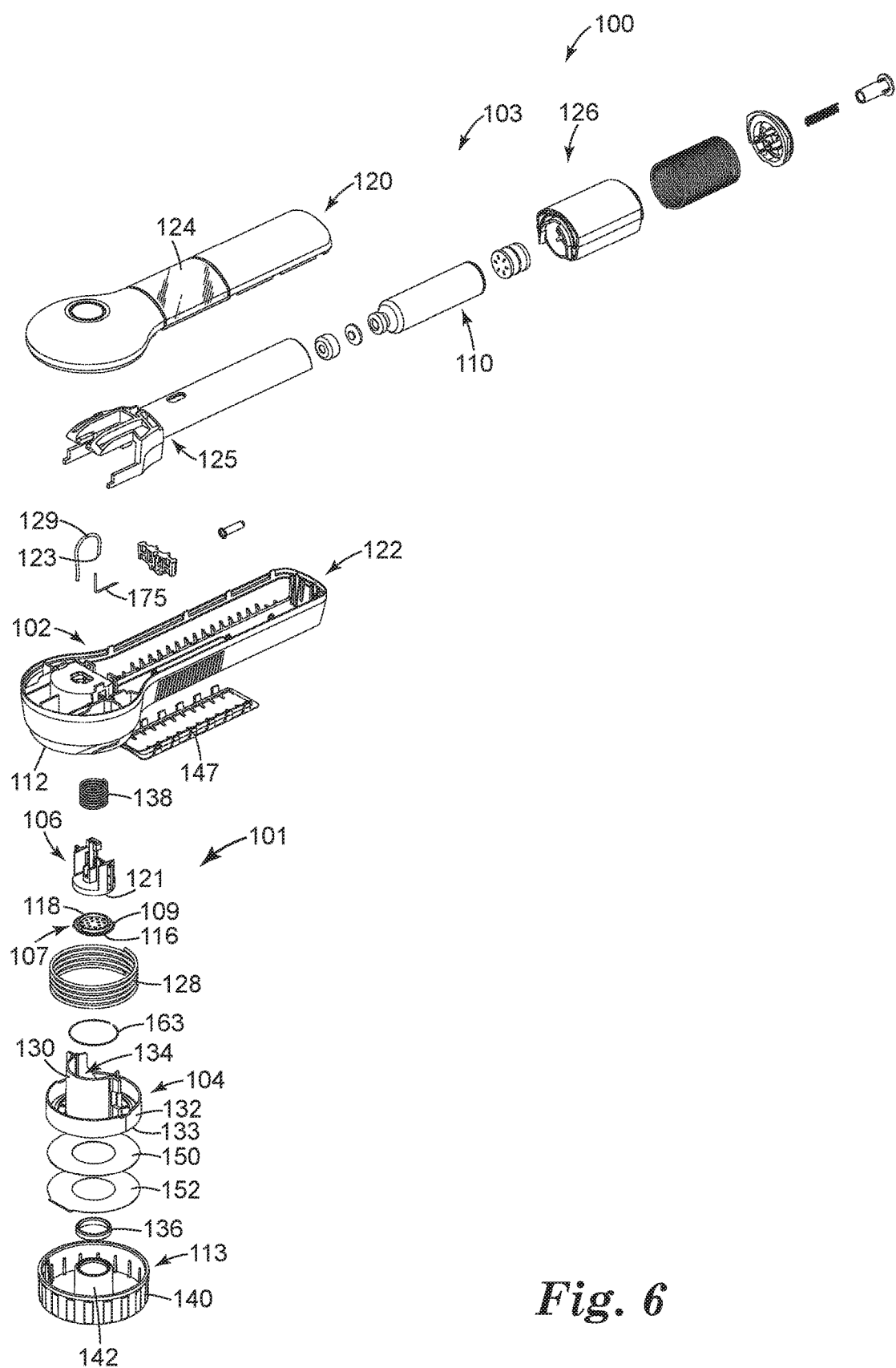
FIG. 6 is a front, top, exploded perspective view of the apparatus of FIGS. 1-5.
Figure 7:
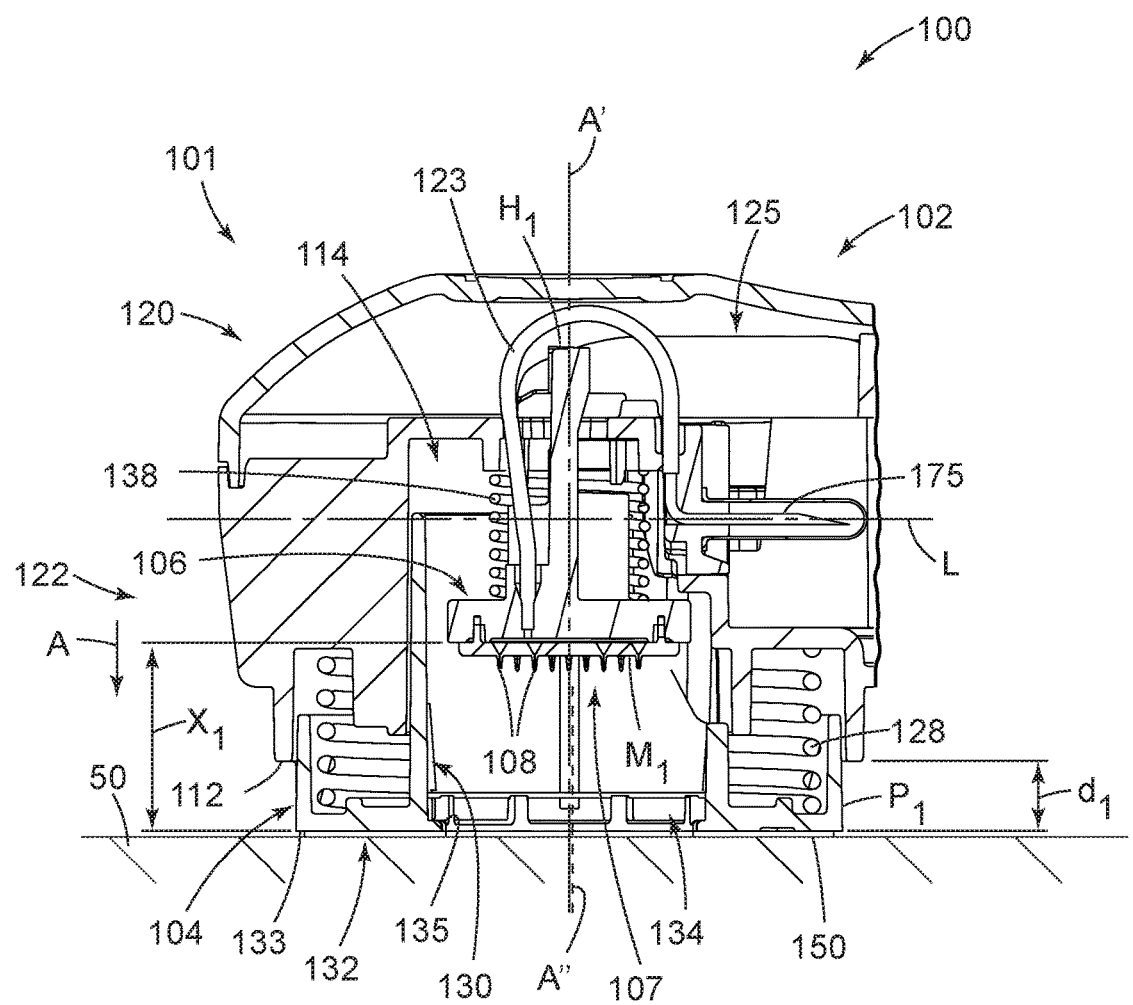
FIG. 7 is a close-up side cross-sectional view of the apparatus of FIGS. 1-6, the apparatus shown in a first condition with the cover removed.

In some embodiments, the housing 102 (e.g., the second portion 122 of the housing 102) can include a base 112 (see, e.g., FIGS. 3-5) configured to be positioned toward a skin surface 50 (see, e.g., FIG. 7). The base 112 may be configured to touch the skin surface 50 during injection and/or infusion and may include a skin-contact adhesive. However, the base 112 of the embodiment illustrated in FIGS. 1-11 does not include an adhesive and is a non-adhesive surface. The base 112 of the housing 102 can extend along the entire length of the housing 102, but the base 112 of the housing 102 referenced herein is particularly referring to the base 112, or portion thereof, that is located adjacent the injection assembly 101 and the actuator 104 that projects outwardly with respect to the base 112, as described in greater detail below. Particularly, the base 112 of the housing 102 referenced herein is generally provided by or defined by a protrusion 119 that protrudes (e.g., downwardly) relative to the remainder of the housing 102 (see FIGS. 4 and 5).

In the accompanying figures, it appears that a rear or tail end of the apparatus 100 (e.g., adjacent the infusion assembly 103 and opposite the injection assembly 101 is located) is raised off of the skin surface 50. While this may be the case, it is certainly possible that the tail end of the apparatus 100 would also rest against the skin surface 50 in use. For example, the rear end of the apparatus 100 can be angled down toward the skin 50 to facilitate resting the rear end on the skin 50. In addition, in some embodiments, the base 112 of the housing 102 in that region (or extending along the length of the apparatus 100) can further include a skin-contact adhesive and can be adhered to the skin. In addition, the protrusion 119 is shown by way of example only; however, it should be understood that the apparatus 100 can be configured not to include such a protrusion 119, and in some embodiments, the entire base 112 of the housing 102 can be flush with the skin 50 or be configured to be adhered to the skin, e.g., after actuation.

The housing 102 can further include or define a cavity (or chamber, or pocket, or recess, etc.) 114. As shown, the base 112 can define an opening 115 that opens into the cavity 114. Said another way, the cavity 114 can extend through the base 112 to define the opening 115. The housing 102, and particularly, the cavity 114 (or a portion thereof) can be configured to house at least a portion of the microneedle array holder 106 and the microneedle array 107 (e.g., when coupled to the holder 106), i.e., prior to application of the microneedles 108 to the skin 50.

The microneedle array holder 106 can be configured to be at least partially located in the cavity 114 of the housing 102 and can be configured to hold a microneedle array 107 within the cavity 114 of the housing 102. The microneedle array holder 106 can also be movable with respect to the housing 102 (i.e., with respect to the opening 115 in the housing 102) to deliver the microneedles 108 to a substrate of interest (e.g., skin). As shown in FIG. 6, the microneedle array holder 106 can include a first (or bottom) side (or base) 121 that can be configured to be positioned toward a skin surface, i.e., skin-facing, and which can be configured to receive the microneedle array 107. By way of example only, a microneedle array 107 can be coupled (e.g., removably coupled) to the microneedle array holder 106 by a variety of coupling means, including but not limited to, press-fit engagement (also sometimes referred to as "friction-fit engagement" or "interference-fit engagement"), snap-fit engagement, magnets, hook-and-loop fasteners, adhesives, cohesives, clamps, stitches, staples, screws, nails, rivets, brads, crimps, detents, welding (e.g., sonic (e.g., ultrasonic) welding), any thermal bonding technique (e.g., heat and/or pressure applied to one or both of the components to be coupled), other suitable coupling means, or combinations thereof.

The "microneedle array" 107 can include the microneedles 108 and any supporting structure or substrate used to support the microneedles 108 and/or to couple the microneedle array 107 to other structures or components of the apparatus 100, such as the microneedle array holder 106. For example, in some embodiments, the "microneedle array" 107 can include a substrate (or "carrier," or "base") 109 from which the microneedles 108 protrude, as well as additional layers or carriers. In the embodiment illustrated in FIGS. 1-11, the microneedles 108 are integrally formed with the substrate 109. However, it should be understood that additional layers can be employed in the microneedle array 107, and other suitable configurations are possible. For example, in some embodiments, the microneedles 108 can be formed directly into the substrate 109 which can then be coupled (e.g., mechanically and fluidly) to a base or additional layer.

In some embodiments, the apparatus 100 does not include the microneedle array 107, but rather, the apparatus 100 can be configured to hold the microneedle array 107 and to deliver the microneedle array 107 to the skin according to specified parameters, e.g., at a predetermined impact velocity and/or force. Such specified parameters, for example, can be used to ensure delivery of the microneedles 108 to a predetermined depth of penetration.

The microneedle array 107 (e.g., the substrate 109) can include a first side 116 comprising the microneedles 108 and a second side 118 opposite the first side 116. The first side 116 can include a first major surface (e.g., defined by the substrate 109 in the illustrated embodiment) from which the microneedles 108 protrude. The first side 116 can be oriented toward the base 112 of the housing 102 (i.e., positioned to face the skin surface 50). That is, a microneedle array 107 can be coupled to the microneedle array holder 106 such that the second side 118 faces the microneedle array holder 106, and the first side 116 is oriented toward the base 112 of the housing 102, i.e., positioned to face the skin surface 50, or be "skin-facing."

The housing 102, the actuator 104, the microneedle array holder 106 and/or the microneedle array 107 (e.g., the substrate 109), the cover 113, and the shuttle 125 can be formed of a variety of materials, including but not limited to, thermoset plastics (e.g., acetal resin available under the trade designation DELRINO DuPont Corporation, Wilmington, Del.; other suitable thermoset plastics, or combinations thereof), thermoplastics (e.g., polyethylene, polypropylene, other suitable thermoplastics, or combinations thereof), or metals (e.g., stainless steel, aluminum, other suitable metals, or combinations thereof), or combinations thereof.

The actuator 104 can include an inner portion 130 configured to be received in (or extend into) the cavity 114 of the housing 102 and to interact and/or engage with the injection assembly 101 and, in some embodiments, the infusion assembly 103. The actuator 104 can further include an outer portion 132 coupled to the inner portion 130 and configured to extend out of the cavity 114 of the housing 102 and through the opening 115 of the housing 102, such that the outer portion 132 can protrude outwardly of the housing 102 and at least partially reside on the exterior of the housing 102 to allow a user to manually manipulate and control the actuator 104. For example, as shown, in some embodiments, the outer portion 132 can include or function as a button or other manually engageable portion or element. The outer portion 132 is illustrated by way of example as being a push-button. By way of further example, the inner portion 130 and the outer portion 132 of the actuator 104 of FIGS. 1-11 are integrally formed.

The actuator 104 can be movable with respect to the housing 102 (e.g., with respect to the opening 115 in the base 112 of the housing 102) and the microneedle array holder 106 between a first position $P_1$ (see FIGS. 3, 4 and 7) and a second position $P_2$ (see FIG. 8) to cause the microneedle array holder 106 to move, respectively, between (i) a first, retracted position $H_1$ (see, FIGS. 3, 4, 7 and 8), in which the microneedle array 107 (when coupled to the microneedle array holder 106) is recessed within the housing 102 (and/or the actuator 104, as described below), such that the microneedle array 107 does not contact the skin 50 when the apparatus 100 is positioned on the skin 50; and (ii) a second, extended (or "impact" or "treatment") position $H_2$ (see FIG. 9), in which at least a portion of the microneedle array 107 (when coupled to the microneedle array holder 106) is positioned to contact the skin 50 (e.g., via the opening 115) when the apparatus is positioned on the skin 50.

In some embodiments, movement of the holder 106 from the retracted position $H_1$ to the extended position $H_2$ can be dampened by one or more dampeners or shock-absorbing elements or materials. For example, as shown in FIG. 6, in some embodiments, the apparatus 100 can include a dampener 163 (e.g., a wire formed into an incomplete circle) that can be positioned between the first side 121 of the microneedle array holder 106 and the actuator 104 (e.g., a base thereof).

As shown, in some embodiments, the actuator 104 can be movable from its first position $P_1$ to its second position $P_2$ against the bias of a biasing element 128. As such, the actuator 104 can be biased in its first position $P_1$ (e.g., downwardly) and can require a user to overcome the bias of the biasing element 128 to actuate the apparatus 100. That is, the biasing force presented by the biasing element 128 represents the force a user would need to overcome in order to actuate the apparatus 100. This biasing force can be controlled so as not to be too high or too low. If the biasing force is too low, the apparatus 100 may be too sensitive and the apparatus 100 may be prematurely actuated, e.g., when a user merely intends to adhere the apparatus 100 to the skin 50. However, if the biasing force is too high, the apparatus 100 may not be able to be actuated by pressing it on soft skin. In some embodiments, the biasing force (e.g., provided by the biasing element 128), and therefore, also the actuation force of the apparatus 100 can be at least 5 N, in some embodiments, at least 6 N, and in some embodiments, is 8 N. In some embodiments, the biasing force (and hence, the actuation force) can be no greater than 15 N, in some embodiments, no greater than 12 N, and in some embodiments, no greater than 10 N.

As shown, the microneedle array holder 106 can be movable between the retracted position $H_1$ and the extended position $H_2$ independently of any portion of the infusion assembly 103, such as the cartridge 110 and the shuttle 125, which can minimize the amount of structure that needs to be moved to impact the skin 50 with the microneedles 108. That is, the injection assembly 103, and portions thereof, is generally not movable with the microneedle array holder 106 between the retracted $H_1$ and the extended position $H_2$. As a result, the injection assembly 101 can be decoupled from and operate separately of the infusion assembly 103, even though both the injection assembly 101 and the infusion assembly 103 can form a portion of the overall apparatus 100, allowing each assembly to be dedicated to their respective functions.

In some embodiments, the infusion assembly 103 (e.g., the shuttle 125 and the cartridge 110) can be configured not to move independently of the housing 102 any appreciable amount in a direction oriented normal or substantially normal with respect to the skin surface 50. That is, in some embodiments, the infusion assembly 103 can be configured not to move independently of the housing 102 toward or away from the skin surface 50 by any appreciable amount. As in the illustrated embodiment, in some embodiments, the infusion assembly 103 may move toward the skin surface 50 with the housing 102 as the apparatus 100 is actuated (e.g., when an inverted actuator 104 is employed), without the infusion assembly 103 moving separately from the housing 102 in this direction. In some embodiments, the infusion assembly 103 can be located in a portion (e.g., an elongated portion, such as a handle or extension) of the apparatus 100 that can be pressed toward the skin surface 50 along with the remainder of the apparatus 100 when the apparatus 100 is pressed toward the skin surface 50 to actuate the actuator 104. Even in such embodiments, the infusion assembly 103 can be configured not to move relative to the housing 102 in a direction toward or away from the skin surface 50.

The first, retracted position $H_1$ and the second, extended position $H_2$ can be spaced a distance from one another along an actuation axis A' (see FIGS. 3 and 7), such that the microneedle array holder 106 is movable along the actuation axis A', e.g., relative to the housing 102 and the actuator 104 (e.g., after the actuator 104 has been moved to its second position $P_2$), between the first, retracted position $H_1$ and the second, extended position $H_2$.

The actuation axis A' can generally be oriented substantially normal with respect to the skin surface 50 (and the first side 121 of the holder 106, as well as the first side 116 of the microneedle array 107 when coupled to the holder 106), but this need not be the case. Rather, in some embodiments, the actuation axis A' can be arcuate or define otherwise nonlinear path(s), etc. The actuation axis A' simply refers to movement between the first, retracted position $H_1$ and the second, extended position $H_2$.

The actuator 104 can further include a base 133 that is configured to be positioned toward the skin surface 50, and a cavity (or chamber, or recess, or pocket, or bore) 134 that extends through the base 133 of the actuator 104 to form an opening 135 (see, e.g., FIG. 7) in the base 133 of the actuator 104. The base 133 can be at least partially defined by the outer portion 132 of the actuator 104, and the cavity 134 can be at least partially defined by the inner portion 130 that is dimensioned to be received in the cavity 114 of the housing 102.

Figure 8:
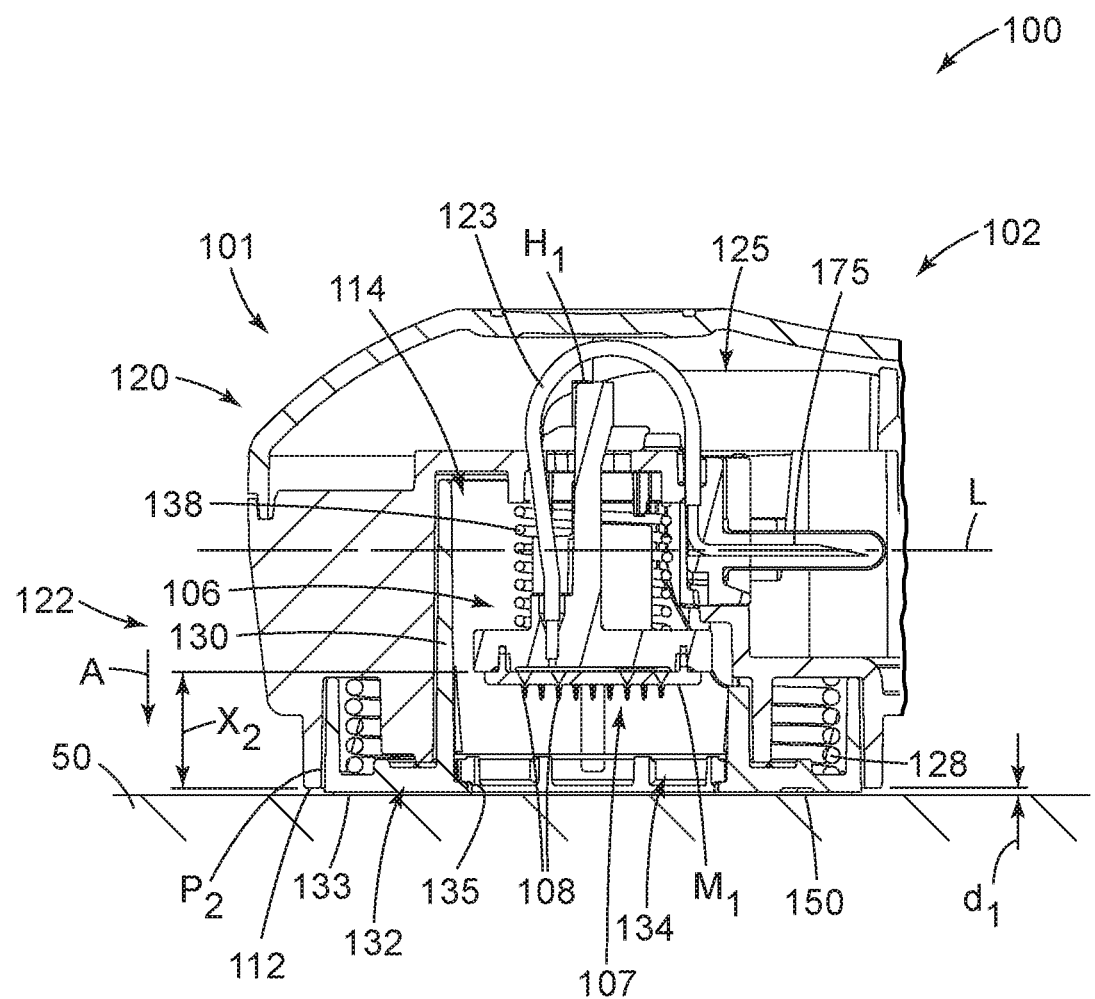
FIG. 8 is a close-up side cross-sectional view of the apparatus of FIGS. 1-7, the apparatus shown in a second condition.

As can be seen by comparing FIGS. 7 and 8, in some embodiments, the actuator 104 (e.g., the base 133 thereof) can be movable with respect to the base 112 of the housing 102, such that when the actuator 104 is in the first position $P_1$, an outermost surface (e.g., the base 133) of the actuator 104 can extend beyond the base 112 of the housing 102 by a first distance $d_1$ (e.g., see FIG. 7); and when the actuator 104 is in the second position $P_2$, the outermost surface of the actuator 104 either no longer extends beyond the base 112 of the housing 102 (e.g., is flush with, or recessed relative to, the base 112), or the outermost surface of the actuator 104 extends beyond the base 112 of the housing 102 by a second distance $d_2$ (e.g., see FIG. 8) that is less than the first distance d$_1$. That is, in some embodiments, the actuator 104 can be movable between the first position P$_1$ and the second position P$_2$ with respect to the base 112 of the housing 102, into and out of the opening 115 formed in the base 112 of the housing 102. Said another way, in some embodiments, when the actuator 104 is in the first position P$_1$, at least a portion of the actuator 104 can protrude from or through the opening 115 in the base 112 of the housing 102 and can define a first surface (e.g., the base 133) configured to be coupled to the skin surface 50. Such a first surface can include a skin-contact adhesive 150, as described below.

The configuration of the actuator 104 is shown by way of example only as being located on a skin-facing surface of the apparatus 100, i.e., adjacent the base 112 of the housing 102. Said another way, the outer (engageable) portion 132 of the actuator 104 is shown as being located on and protruding from a lower portion (i.e., the second portion 122) of the housing 102. That is, the actuator 104 is an example of an 'inverted actuator,' as compared to conventional systems, where the actuator 104 is located on an underside of the apparatus 100. Such a configuration allows for facile operation of the apparatus 100 and particularly allows for the actuator 104 to be moved from the first position P$_1$ to the second position P$_2$ in response to the apparatus 100 being pressed toward the skin surface 50 by pressing on a non-skin-facing, or upper, portion of the apparatus 100. Such a non-skin-facing, or upper, portion of the apparatus 100 (e.g., of the housing 102) need not be located directly opposite the actuator 104. That is, the non-skin-facing, or upper, portion can be located in an off-axis position with respect to a central longitudinal or actuation axis of the actuator 104. Such an 'inverted actuator' is further described in PCT Publication No. WO2014/193729, which is incorporated herein by reference.

The term "off-axis" generally refers to a position, direction, or axis of movement, that is not aligned with the central longitudinal or actuation axis of the actuator 104. For example, the actuator 104 can move from the first position P$_1$ to the second position P$_2$ in a first direction, along an actuation axis A" (see FIG. 7), which, in the embodiment illustrated in FIGS. 1-11, is also its central longitudinal axis. Such actuation or movement of the actuator 104 can be caused by a force exerted along a second direction that is not directly opposite the second direction or that is not aligned with the actuation axis A" of the actuator 104. Rather, such movement of the actuator 104 can be caused by a force that is oriented at an oblique angle with respect to the actuation axis A" of the actuator 104. In some embodiments, the second direction or axis can intersect the first direction or the actuation axis A" of the actuator 104 (e.g., at an oblique angle), or the second direction or axis can be parallel with respect to the central longitudinal axis of the actuator 104 without being directly in line with the actuation axis A".

By allowing for off-axis actuation of the apparatus 100, the apparatus 100 can offer more reliable actuation, enhanced user comfort and enhanced ergonomics, for example, if the apparatus 100 can be actuated without requiring that a user engage or manipulate a specific location or element on the apparatus 100. For example, at least a portion (e.g., the first (upper) portion 120 of the housing 102) can be configured to be pressed toward the skin 50 using any portion of a hand, such as a user's palm or fist, as opposed to requiring the precise dexterity of finger manipulation. Such a configuration can provide an advantage, for example, for arthritic and/or elderly patients. In addition, off-axis actuation allows for actuation of the apparatus 100 in a variety of ways, as opposed to only a single option, that are clearly understood by a user, e.g., by an intuitive design or configuration.

While the 'inverted actuator' 104 of the illustrated embodiment is shown as also providing the opening 135 through which the microneedle array 107 will be deployed to impact and penetrate a skin surface, in some embodiments, an inverted actuator can still be employed, i.e., on an underside or skin-facing side of the apparatus 100 and housing 102, without the actuator 104 also defining a cavity 134 or opening 135 through which the microneedle array 107 and microneedle array holder 106 move (as is the case in the illustrated embodiment, as described below). That is, in some embodiments, the actuator 104 can still be inverted but not positioned directly adjacent the opening through which the microneedles 108 extend when the microneedle array holder 106 is in its extended position H$_2$. Particular advantages, however, can result from employing an actuator 104 such as that illustrated where the microneedle array holder 106 is movable within the cavity 134 of the actuator 104 as well, such as a compact design.

In some embodiments, as shown in the illustrated embodiment, the actuator 104 can be configured so as to be located only in a portion of the apparatus 100, which can localize the actuation of the apparatus 100 to a precise area, even without requiring precise user manipulation to actuate the apparatus 100. For example, as shown, in some embodiments, the overall apparatus 100 can have or define a first footprint having a first area, and the actuator 104 can have a second footprint having a second area, and the second area can be less than the first area. In some embodiments, the second area can be less than half (i.e., less than 50%) of the first area. In some embodiments, the second area can be less than a quarter (i.e., less than 25%) of the first area.

As shown in FIGS. 1-6 and 10-11, the cover 113 can be configured to cover the opening 115 in the base 112 of the housing 102. As shown in FIGS. 3-6 and described in greater detail below with respect to FIGS. 10 and 11, in some embodiments, the cover 113 can be a 'dual cover' that includes a first portion 140 configured to cover at least a portion of the base 112 of the housing 102 adjacent the opening 115, and a second portion 142 configured to be at least partially received in the cavity 114 of the housing 102 and further configured to cover the plurality of microneedles 108 on the microneedle array 107. In embodiments such as the illustrated embodiment that employ an 'inverted actuator' 104, the cover 113 can further be configured to cover the opening 135 to the cavity 134 of the actuator 104 (see, e.g., FIG. 3). The cover 113 (e.g., the second portion 142 thereof) can be configured to maintain the sterility of the microneedles 108 and the fluid path 123 (i.e., in embodiments employing the infusion assembly 103). In embodiments in which the microneedle array 107 will be deployed via the opening 135 in the actuator 104, the cover 113 (e.g., the first portion 140 thereof) can also be configured to cover and protect the actuator 104 prior to use, and can be used to inhibit or prevent accidental premature actuation of the actuator 104. In embodiments in which the microneedle array 107 will deployed via the opening 115 in the housing 102 but not necessarily the opening 135 in the actuator 104, the cover 113 (e.g., the first portion 140 thereof) can be configured to cover and protect at least the portion of the base 112 of the housing 102 that is configured to be coupled to a skin surface.

Figure 4:
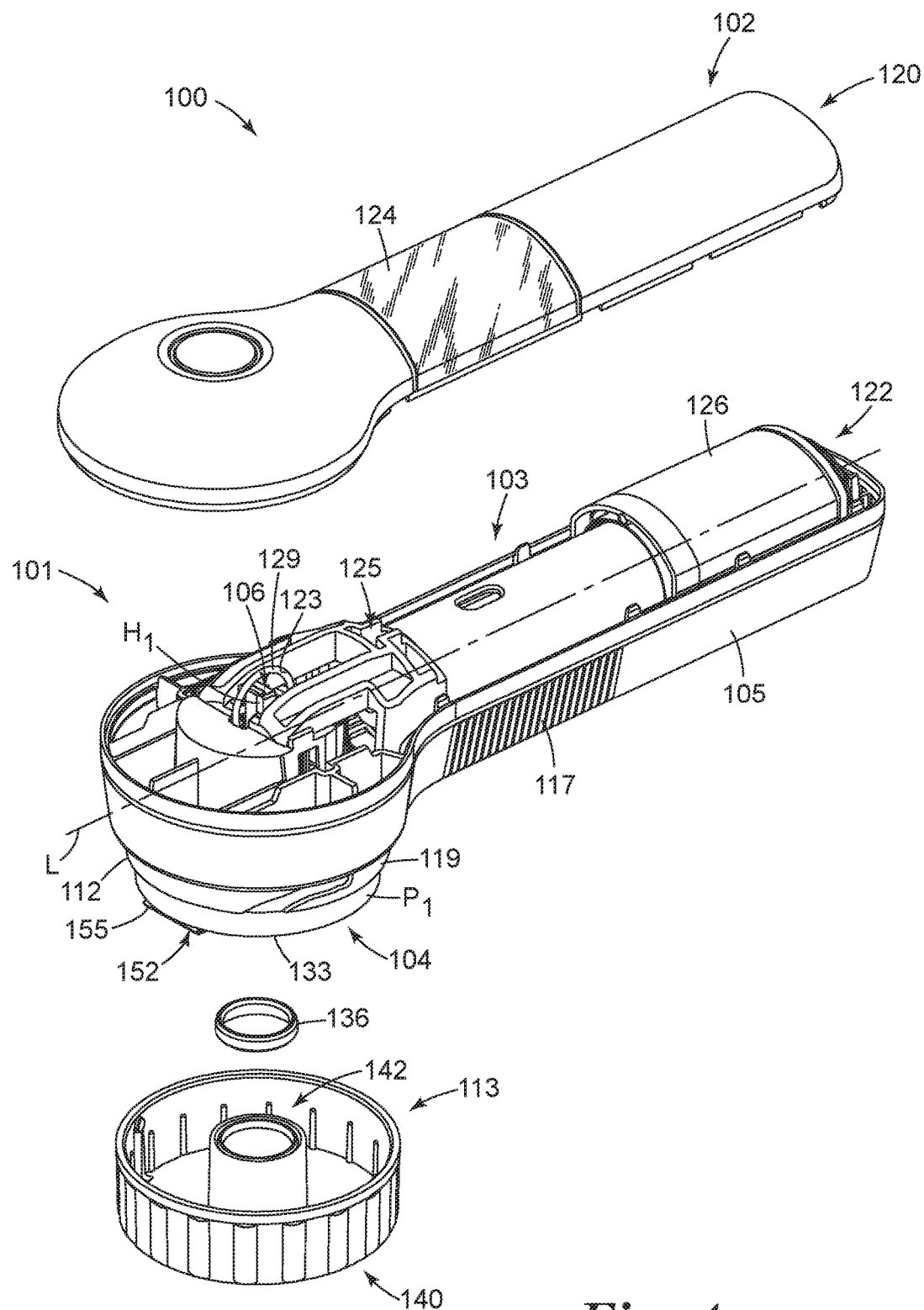
FIG. 4 is a front, top, partially exploded perspective view of the apparatus of FIGS. 1-3.
Figure 5:
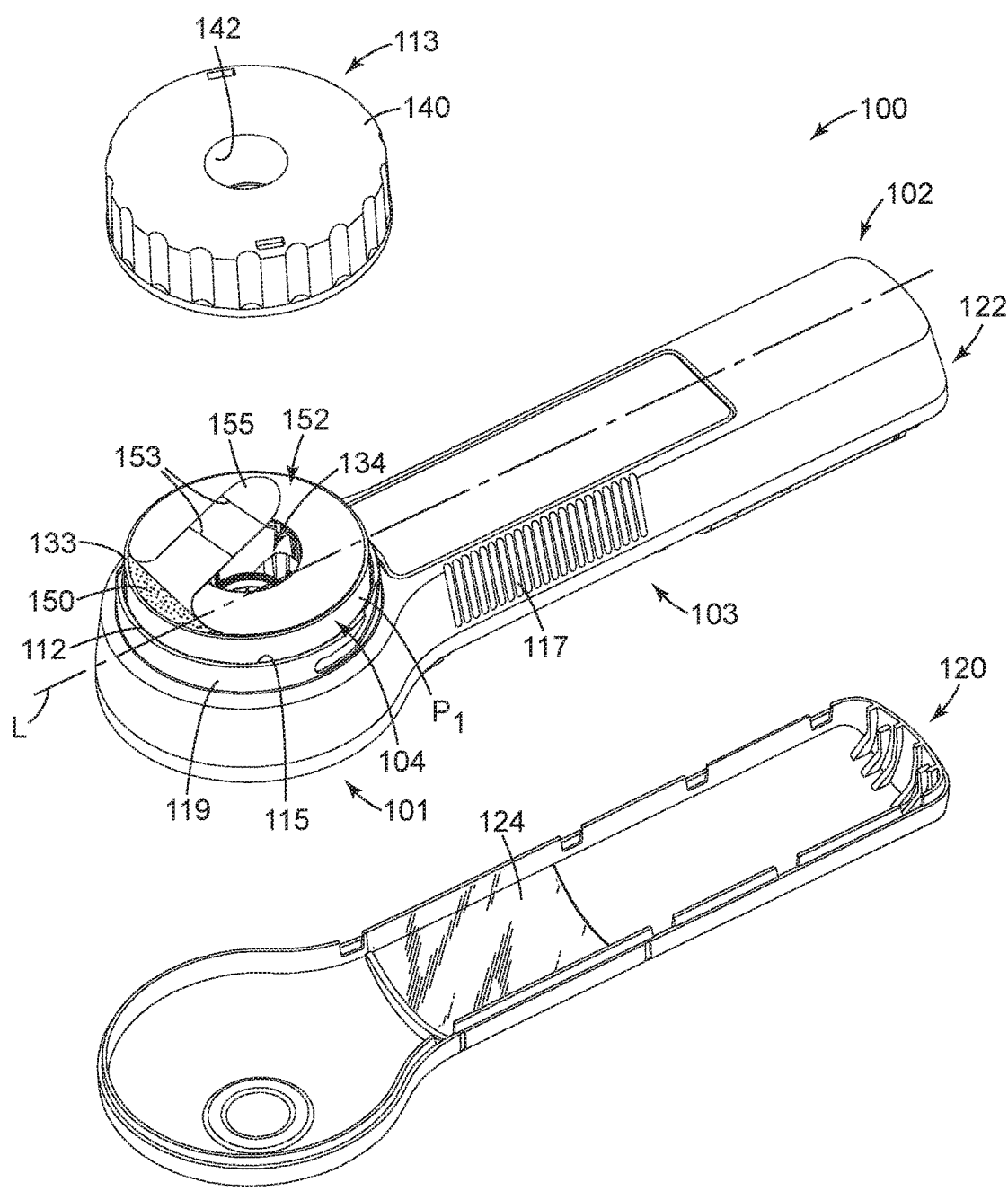
FIG. 5 is a front, bottom, partially exploded perspective view of the apparatus of FIGS. 1-4.

As shown in FIG. 5, in some embodiments, the base 133 of the actuator 104 can include the skin-contact adhesive 150 (described in greater detail below), and the apparatus 100 can further include an optional release liner 152 (described in greater detail below), which can protect the skin-contact adhesive 150 prior to use and during assembly, storage and shipment of the apparatus 100. The release liner 152 can be removed prior to applying the apparatus 100 to skin. The release liner 152 can be configured to release, or can be configured to present release characteristics to, the skin-contact adhesive 150, so that the apparatus 100 can be coupled to the release liner 152 during storage and shipment, and can be easily separated from the release liner 152 during application of the apparatus 100. By way of example only, the release liner 152 can include a tab 155 (see FIGS. 4 and 5) positioned to facilitate removing the release liner 152 from the skin-contact adhesive 150 when desired. As shown, the tab 155 can include one or more folds 153 to allow the tab 155 to be shortened during storage but lengthened when desired to facilitate removal of the release liner 152.

In use, the release liner 152 can be removed (if employed) from the skin-contact adhesive 150, and the adhesive base 133 of the actuator 104 can be coupled to the skin 50. Actuation of the actuator 104 can occur immediately following coupling of the base 133 of the actuator 104 to the skin 150 or even substantially simultaneously with coupling the base 133 to the skin 150. The base 133 of the actuator 104 (or the base 112 of the housing 102, if the skin-facing actuator 104 is not employed) can remain coupled to the skin 50 throughout injection and, optionally, infusion. As a result, in some embodiments, the apparatus 100 can be configured to be "worn" by a patient during infusion/injection of fluid into the skin 50. In such embodiments, the apparatus 100 may be directly applied to a patient's skin 50 to accommodate ambulatory movement while keeping the microneedles 108 at an appropriate penetration depth(s). That is, even in embodiments in which the housing 102 itself does not include the skin-contact adhesive 150, the housing 102 (i.e., the apparatus 100 as a whole, including the actuator 104, the housing 102, and the elements of the infusion assembly 103) can be configured to remain coupled to the skin surface 50 after the microneedle array 107 has punctured the skin 50 and during infusion. For example, in such embodiments, the housing 102 can be configured to be adhered to the skin 50 via the skin-contact adhesive 150 on the actuator 104.

In embodiments in which the actuator 104 is not located on an underside or on a skin-facing portion of the apparatus 100 (or housing 102), the base 112 of the housing 102 can include the skin-contact adhesive 150 and optional release liner 152. In addition, any description herein regarding positioning the base 133 of the actuator 104 on the skin surface 50 can instead be interpreted to be referring to positioning the base 112 of the housing 102 on the skin surface 50. Similarly, any description regarding movement of the microneedle array holder 106 within the cavity 134 of the actuator 104 may still apply if the actuator 104 is not located on a skin-facing portion of the apparatus 100, depending on the relative configuration of these components. Furthermore, in embodiments in which the actuator 104 is inverted as shown in the illustrated embodiment, the base 133 of the actuator 104 can be configured to contact (and adhere to, via the skin-contact adhesive 150) the skin 50 when the apparatus 100 is positioned on the skin surface 50. In embodiments in which the actuator 104 is not inverted, the base 112 of the housing 102 can be configured to contact (and adhere to) the skin 50 when the apparatus 100 is positioned on the skin surface 50.

In some embodiments, as shown, the microneedle array holder 106 can be located in and movable in the cavity 134 of the actuator 104 between the retracted position $H_1$ and the extended position $H_2$. As such, in some embodiments, the actuator 104 can be configured to at least partially surround the microneedle array 107 when the microneedle array 107 is coupled to the holder 106, at least when the holder 106 is in the extended position $H_2$. In some embodiments, the actuator 104 can be configured such that at least a portion of the actuator 104 (e.g., the outer portion 132) surrounds the microneedle array 107 (and/or the microneedle array holder 106) on all sides, or encircles the microneedle array 107 (and/or the microneedle array holder 106), at least when the microneedle array holder 106 is in the extended position $H_2$.

As shown in FIGS. 7 and 8, in embodiments in which the actuator 104 is inverted and located adjacent the same opening 115 through which the microneedle array 107 will contact the skin 50, and when the actuator 104 is in the first position $P_1$ and the microneedle array holder 106 is in the retracted position $H_1$, the base 133 of the actuator 104 can be positioned a first distance $x_1$ from the first side (or base) 121 of the microneedle array holder 106 (and/or the first side (or base) 116 of the microneedle array 107)—see FIG. 7. When the actuator 104 is in the second position $P_2$, the base 133 of the actuator 104 can be positioned a second distance $x_2$ from the first side (or base) 121 of the microneedle array holder 106 (and/or the first side (or base) 116 of the microneedle array 107)—see FIG. 8—and the second distance $x_2$ can be less than the first distance $x_1$. As a result, the distance between the base 133 of the actuator 104 and the first side 121 of the microneedle array holder 106 (or the first side 116 of the microneedle array 107) can decrease when the actuator 104 is moved from the first position $P_1$ to the second position $P_2$.

By way of example only, in the embodiment illustrated in FIGS. 1-11, at least a portion of the cavity 114 in the housing 102 can have the shape of a cylindrical bore, at least a portion of the actuator 104 can include an annular cross-sectional shape (e.g., when the cross-section is taken substantially parallel with respect to the base 133), and the inner portion 130 of the actuator 104 can be substantially tubular in shape and be dimensioned to be received in the cylindrical bore-shaped cavity 114 of the housing 102. In addition, the cavity 134 defined at least partially by the inner portion 130 of the actuator 104 can have the shape of a cylindrical bore. By way of example only, the central longitudinal axes of the bore-shaped cavities 114 and 134 defined by the housing 102 and the actuator 104, respectively, can be substantially aligned, and the actuation axis A' (see FIGS. 3 and 7) of microneedle array holder 106 can also be substantially aligned with the central longitudinal axes of the cavities 114 and 134.

In some embodiments, the actuation axis A' and the central longitudinal axes of the cavities 114 and 134 may not all be exactly aligned but can be substantially parallel with respect to one another. In some embodiments, the actuation axis A' of the holder 106 can be oriented substantially parallel with respect to the actuation axis A" of the actuator 104, as shown in the illustrated embodiment. Furthermore, in some embodiments, as shown, the actuation A' of the holder 106 can be substantially aligned (i.e., in line with) with the actuation axis A" of the actuator 104.

When the microneedle array holder 106 is in the first, retracted position $H_1$, the holder 106 can be recessed within the housing 102 and the actuator 104, such that the holder 106 (and the microneedle array 107, when coupled to the holder 106) does not extend beyond the base 112 of the housing 102 or the base 133 of the actuator 104. The microneedle array 107 can be movable with the holder 106 along the entire distance between the holder's retracted and extended positions $H_1$ and $H_2$. That is, when the microneedle array holder 106 is in the first, retracted position $H_1$ and a microneedle array 107 is coupled to the holder 106, the microneedle array 107 can also be in a first, retracted position $M_1$ (see, e.g., FIGS. 3, 7 and 8), e.g., in which the microneedle array 107 is recessed within the housing 102 and the actuator 104 such that the microneedle array 107 does not contact (or is not positioned to contact) the skin surface 50 when the base 133 of the actuator 104 (or the base 112 of the housing 102 in embodiments in which the actuator 104 is located in a different location than adjacent the base 112 of the housing 102) is positioned on the skin surface 50. The microneedle array 107 can be housed within the cavity 114 of the housing 102 and the cavity 134 of the actuator 104, and can be recessed with respect to the base 112 of the housing 102 and the base 133 of the actuator 104 in its retracted position $M_1$.

Furthermore, when the microneedle array holder 106 is in the second, extended position $H_2$ and a microneedle array 107 is coupled to the holder 106, the microneedle array 107 can also be in a second, extended position $M_2$ (see, e.g., FIG. 9), e.g., in which at least a portion of the microneedle array 107 is positioned to contact the skin surface 50 when the base 133 of the actuator 104 is positioned on the skin surface 50.

When the microneedle array holder 106 and the microneedle array 107 are in their respective second positions $H_2$ and $M_2$ (see FIG. 9), at least a portion of the microneedle array 107 (and, potentially, a portion of the microneedle array holder 106) can extend beyond the base 133 of actuator 104 (or the base 112 of the housing 102 if an inverted actuator 104 is not employed). However, this need not be the case, and in some embodiments, it can be preferred for this not to be the case. Rather, in some embodiments, the microneedles 108 can be positioned close enough to the base 133 of the actuator 104 (while still being recessed within the housing 102 and the actuator 104 and without extending beyond the base 133 of the actuator 104), such that when the base 133 is pressed onto the skin surface 50, the skin 50 is caused to deform or dome up through the opening 135 of the actuator 104 and into the cavity 134 to a position where the skin 50 is contacted by the microneedles 108.

Portions of the housing 102 defining the cavity 114 and/or portions (e.g., the inner portion 130) of the actuator 104 defining the cavity 134 can retain and/or guide the microneedle array holder 106 for displacement along a path generally perpendicular to the base 133 of the actuator 104 (and/or the base 112 of the housing 102), as indicated by arrow A in FIG. 7. The actuation axis A' of the microneedle array holder 106 can be generally normal or perpendicular to that of the longitudinal axis L of the apparatus 100. While in one exemplary embodiment, the motion of holder 106 may be at substantially 90 degrees with respect to the base 133 (and/or the base 112), it will be appreciated that the generally normal path may deviate from 90 degrees to assume orientations that can penetrate deep enough to deliver an intended dosage.

The microneedle array holder 106 (and a microneedle array 107 coupled thereto) can be movable from the retracted position $H_1$ (and $M_1$) to the extended position $H_2$ (and $M_2$) by a first stored energy device 138 that is actuatable to release its potential energy for applying force to the microneedle array holder 106 in a direction generally normal to the base 133 (and/or the base 112), for example, downwardly, toward the skin surface 50. In some embodiments, such actuated force allows for movement of the holder 106 in a controlled manner, thereby ensuring application of the necessary forces for the microneedles 108 to penetrate the skin of a patient. As a result, the apparatus 100 can reliably and consistently deliver the microneedle array 107 to the skin at a desired impact velocity, e.g., to achieve the desired depth(s) of penetration.

In some embodiments, the first stored energy device 138 can be actuatable to apply force to the holder 106 to achieve a velocity of the microneedle array 107 before impact (i.e., before the microneedle array 107 held by the holder 106 impacts a patient's skin) ranging from between about 2 and about 20 m/s. More typically, the microneedle array 107 can strike a patient's skin at a velocity before impact ranging from between about 4 and about 12 m/s, in some embodiments, at a velocity before impact of at least 5 m/s, and in some embodiments, at a velocity before impact of about 6 m/s.

In some embodiments, the first stored energy device 138 can include a biasing element (e.g., a spring), and is shown as a coil spring by way of example only in the illustrated embodiment. However, stored energy devices of the present disclosure can include at least one stored energy device from a group consisting of: biasing elements (e.g., springs), propellants, chemicals, motors, electrical devices, and combinations thereof.

The microneedle array holder 106 is biased downwardly in the apparatus 100, toward its extended position $H_1$. As a result, the microneedle array 107, when coupled to the holder 106 is also biased toward its extended position $M_1$. The microneedle array holder 106 is primed, or held under load or against the bias (e.g., when a biasing element is employed as the stored energy device 138) when in the retracted position $H_1$, such that when the microneedle array holder 106 is released from being held, the stored energy device 138 will provide the forces to move the microneedle array holder 106 to its extended position $H_2$, and particularly, at a desired velocity.

In some embodiments, a portion of the actuator 104 can hold the microneedle array holder 106 in its retracted position $H_1$ until the actuator 104 has been moved to its second position $P_2$, at which point the actuator 104 no longer holds the microneedle array holder 106, and the microneedle array holder 106 is free to be driven by the stored energy device 138.

However, in some embodiments, as shown in the illustrated embodiment, an intermediate component, i.e., between the actuator 104 and the holder 106, can be actuated to move (or be released) by moving the actuator 104 to its second position $P_2$, and when that intermediate component is actuated or allowed to move, it moves to a position in which it no longer retains the holder 106 in its retracted position $H_1$, and the microneedle array holder 106 is free to be driven by the stored energy device 138. As a result, in some embodiments, the microneedle array holder 106 is held within the housing 102 in its retracted position $H_1$ by an element, component or structure of the apparatus 100 other than the actuator 104.

In the illustrated embodiment, that intermediate component is an element of the infusion assembly 103, namely, the shuttle 125. Additional details regarding shuttle movement and the process of delivering an active agent from the on-board infusion assembly 103 can be found in PCT Publication Nos. WO2014/193729 and WO2014/193725, which are each incorporated herein by reference.

In use, the cover 113 and release liner 152 can be removed. The skin-contact adhesive 150 on the base 133 of the actuator 104 (and/or on the base 112 of the housing 102)

can be applied to the skin 50. An upper portion (e.g., the first portion 120) of the housing 102 of the apparatus 100 can be pressed toward the skin 50 to cause the actuator 104 to move from its first position $P_1$ (as shown in FIG. 7, which illustrates a first condition of the apparatus 100) to its second position $P_2$ (as shown in FIG. 8, which illustrates a second condition of the apparatus 100), e.g., against the bias of the biasing element 128.

Figure 9:
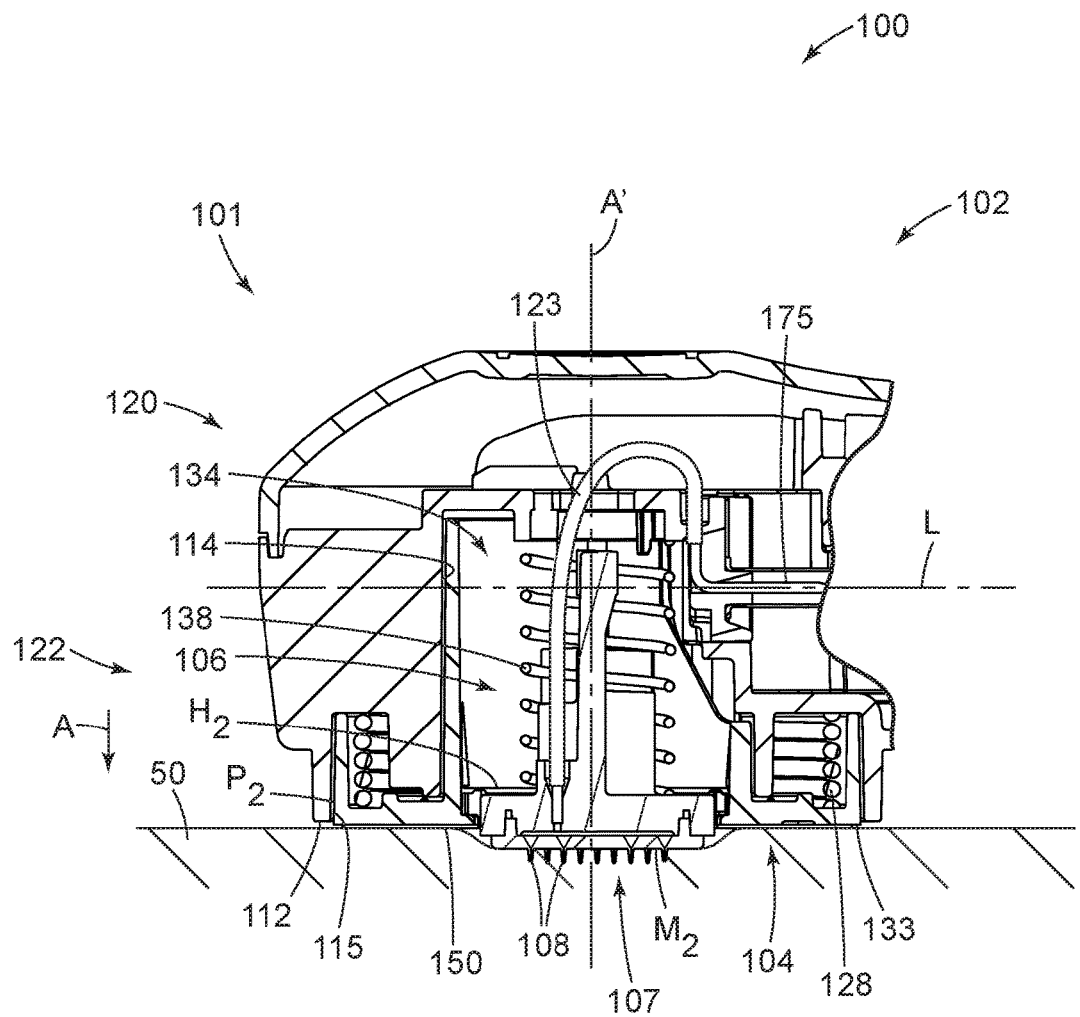
FIG. 9 is a close-up side cross-sectional view of the apparatus of FIGS. 1-8, the apparatus shown in a third condition.

Movement of the actuator 104 to its second position $P_2$ can directly or indirectly release the microneedle array holder 106. For example, movement of the actuator 104 to its second position $P_2$ can release the shuttle 125, such that the shuttle 125 is no longer positioned to retain the microneedle array holder 106 in its retracted position $H_1$, such that the holder 106 is released, and the first stored energy device 138 can begin to provide forces to drive the microneedle array holder 106 to its extended position $H_2$, and accordingly, the microneedle array 107 to its extended position $M_2$ (as shown in FIG. 9, which illustrates a third condition of the apparatus 100).

Figure 10:
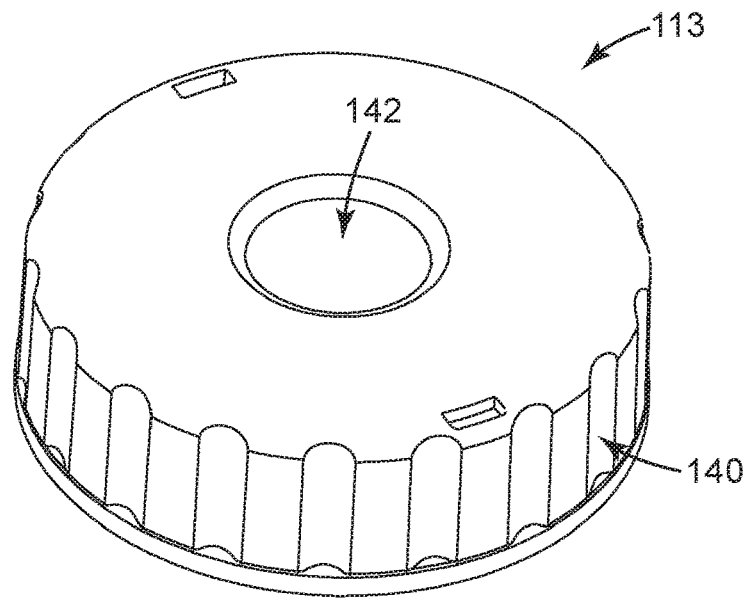
FIG. 10 is a top perspective view of the cover of FIGS. 1-6.
Figure 11:
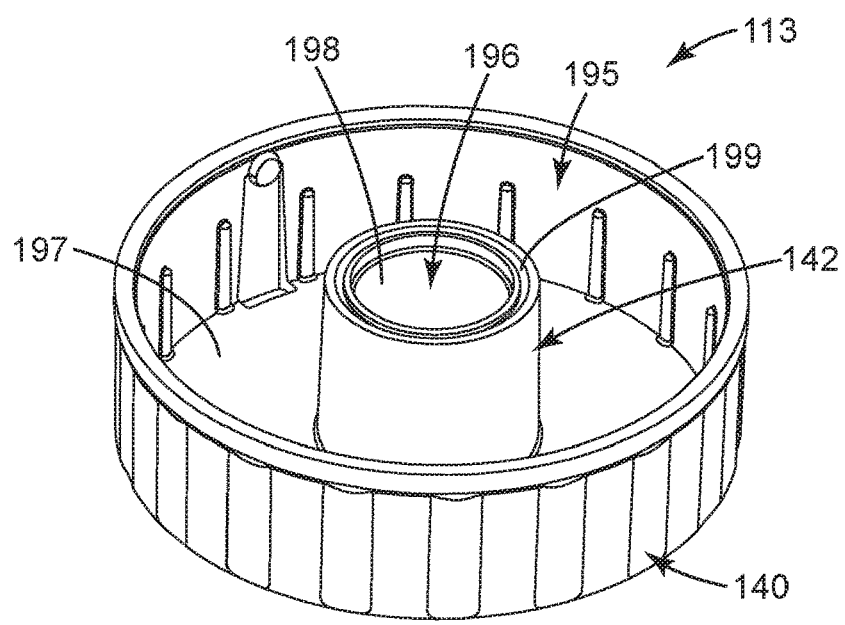
FIG. 11 is a bottom perspective view of the cover of FIGS. 1-6 and 9.

FIGS. 10 and 11 illustrate the cover 113 in greater detail. As mentioned above, the cover 113 can include (i) a first (e.g., outer) portion 140 configured to cover at least a portion of the base 112 of the housing 102 adjacent the opening 115, as well as the base 133 of the actuator 104; and (ii) a second (e.g., inner) portion 142 configured to be received in the cavity 114 of the housing 112 and further configured to cover the plurality of microneedles 108 on the microneedle array 107 when the microneedle array holder 106 is in the retracted position $H_1$. The second portion 142 can also be configured to be received in the cavity 134 of the actuator 104, e.g., in embodiments employing an inverted actuator 104 through which the microneedle array 107 is deployed. In addition, the first portion 140 can cover the base 133 of the actuator 104 adjacent the opening 135 in embodiments employing an inverted actuator 104 through which the microneedle array 107 is deployed.

As mentioned above, the base 133 of the actuator 104 and/or the base 112 of the housing 102 can include the skin-contact adhesive 150 and any optional release liners 152. In such embodiments, the cover 113 (i.e., the first portion 140 thereof) can be configured to cover at least the portion of the base 133 (and/or the base 112) including the skin-contact adhesive 150 and, optionally, any release liners 152 employed, particularly when the actuator 104 is in the first position $P_1$. However, in some embodiments, after the apparatus 100 has been used and removed from the skin 50, the cover 113 can be used to re-cover the actuator 104 and the base 112 of the housing 102, with the actuator 104 in its second position $P_2$.

In the illustrated embodiment, the first portion 140 and the second portion 142 of the cover 113 are integrally formed together. However, in some embodiments, the first and second portions 140 and 142 can be removably coupled together, which can allow the base 133 (and/or the base 112) to be covered and/or uncovered independently of the microneedles 108.

By way of example only, the second portion 142 is illustrated as being generally tubular in shape, such that the second portion 142 can extend through the opening 135 (and/or the opening 115) in the base 133 (and/or the base 112) and into the cavity 134 of the actuator 104 (and/or the cavity 114 of the housing 112).

As shown in FIG. 10, the first portion 140 can include or define a recess (or chamber or pocket) 195 (i.e., with a closed end 197) dimensioned to receive at least a portion of the base 133 of the actuator 104 and/or at least a portion of the base 112 of the housing 102. In embodiments in which the cover 113 covers the actuator 104, the closed end or base 197 of the recess 195 can be spaced a distance from the base 133 of the actuator 104 when the cover 113 is coupled to the apparatus 100, such that the actuator 104 is not undesirably or prematurely actuated 104 prior to use.

As further shown, the second portion 142 can include or define a recess (or chamber or pocket) 196 (i.e., with a closed end 198) dimensioned to receive the plurality of microneedles 108 protruding from the first major surface of the first side 116 of the microneedle array 107. The recess 196 (e.g., the closed end 198) in the second portion 142 can be at least partially defined by an inner surface, and the inner surface of the recess 196 and the first side 116 of the microneedle array 107 can together define a sterile chamber for housing the plurality of microneedles 108 after assembly of the apparatus 100 and prior to use. Such a sterile chamber can allow sterilizing agent(s) free access to the enclosed volume, while keeping contaminants from entering the chamber post-sterilization.

As further shown in FIG. 10, in some embodiments, the second portion 142 of the cover 113 can include at least one of a projection and a recess, and the first side 116 of the microneedle array 107 (and/or the first side 121 of the holder 106) can include at least one of a recess and a projection, respectively, dimensioned to receive the projection and/or project into the recess of the second portion 142 of the cover 113. Such an arrangement can allow the second portion 142 to matingly engage with the microneedle array 107 (and/or the holder 106) and to facilitate housing and protecting the microneedle array 107 with the second portion 142 of the cover 113.

As shown in FIGS. 3 and 10, in the illustrated embodiment, a microneedle-facing (e.g., an upwardly-facing) recess 199 is illustrated in the second portion 142 of the cover 113 by way of example. As shown, the first side 116 of the microneedle array 107 can include a cover-facing (e.g., a downwardly-facing) recess 139 that surrounds the plurality of microneedles 108. As shown in FIGS. 3, 4 and 6, a sealing member 136 can be employed that is dimensioned to be received in the recess 199 in the second portion 142 of the cover 113 and the recess 139 in the microneedle array 107 to seal or close the chamber configured to house the microneedles 108 and to provide additional spacing between the closed end 198 of the recess 196 of the second portion 142 of the cover 113 and the first side 116 of the microneedle array 107. This specific arrangement is shown by way of example only, but generally, the second portion 142 of the cover 113 can be configured to be coupled in some way to the first side 116 of the microneedle array 107 (and/or the first side 121 of the holder 106) to enclose and protect the plurality of microneedles 108 prior to use, i.e., to maintain the sterility of the microneedles 108. In some embodiments, the sealing member 136 and/or a portion of the cover 113 can be permeable to sterilizing agent(s)) while inhibiting contaminants from entering the chamber after sterilization. In some embodiments, the second portion 142 can include or provide the sealing member 136. In such embodiments, the sealing member 136 may be integrally formed with the cover 113 and configured to be coupled to at least one of the first side 116 of the microneedle array 107 and the first side 121 of the microneedle array holder 106.

As mentioned above, the housing 102 can include a protrusion 119 that defines or includes the base 112. The actuator 104 (e.g., the outer portion 132 thereof) can extend outwardly (e.g., downwardly) from the protrusion, e.g., when the actuator 104 is in its first position $P_1$. The recess 195 in the first portion 140 of the cover 113 can be dimensioned to receive the protrusion of the housing 119 and/or at least a portion of the outer portion 132 of the actuator 104.

The cover 113 can be configured to be coupled to the housing 102 (e.g., the protrusion 119) and/or the actuator 104 by any of the coupling means described above. The cover 113 can also be configured to abut a portion of the housing 102 from which the protrusion 119 projects, which can facilitate inhibiting the cover 113 from pressing the actuator 104 when the cover 113 is coupled to the apparatus 100 to prevent premature actuation of the actuator 104.

While the embodiment of FIGS. 1-11 employs a specific configuration and arrangement of elements to accomplish injection, it should be understood that variations to the specific structures and arrangements shown in the illustrated embodiment are within the spirit and scope of the present disclosure.

The following descriptions of the application time, microneedles, skin-contact adhesive, release liners, and active agents can apply to any embodiment of the apparatuses of the present disclosure.

In some embodiments, the length of time that apparatuses of the present disclosure can remain on the skin 50 may be an extended time, however, apparatuses of the present disclosure are more likely to remain on the skin 50 for shorter durations of time. For example, in some embodiments, apparatuses of the present disclosure can remain on the skin for a treatment period of at least 1 second, in some embodiments, at least 5 seconds, in some embodiments, at least 10 seconds, in some embodiments, at least 15 seconds, and in some embodiments, at least 30 seconds. In some embodiments, the apparatus can remain on the skin for a period of time of no greater than 1 hour, in some embodiments, no greater than 30 minutes, in some embodiments, no greater than 20 minutes, in some embodiments, no greater than 10 minutes, and in some embodiments, no greater than 5 minutes. In some embodiments, the apparatuses can remain on the skin for a treatment period of from 1 second to 1 hour, in some embodiments, from 10 seconds to 10 minutes, and in some embodiments, from 30 seconds to 5 minutes.

In some embodiments, the apparatus 100 can be configured to deliver an active agent over an infusion period of at least 1 second, in some embodiments, at least 5 seconds, in some embodiments, at least 10 seconds, in some embodiments, at least 15 seconds, and in some embodiments, at least 30 seconds. In some embodiments, apparatuses of the present disclosure can include infusion periods of no greater than no greater than 1 hour, in some embodiments, no greater than 30 minutes, in some embodiments, no greater than 20 minutes, in some embodiments, no greater than 10 minutes, and in some embodiments, no greater than 5 minutes. In some embodiments, the apparatuses can remain on the skin for a treatment period of from 1 second to 1 hour, in some embodiments, from 10 seconds to 10 minutes, and in some embodiments, from 30 seconds to 5 minutes.

Skin-Contact Adhesive

In some embodiments, the skin-contact adhesive 150 can cover the entire base 133 of the actuator 104 (and/or the base 112 of the housing 102). Alternatively, in some embodiments, the skin-contact adhesive 150 can partially cover the base 133 (and/or the base 112), e.g., including intermittent application of the skin-contact adhesive 150 to create gaps (e.g., randomly, or in a pattern), and/or a complete ring of skin-contact adhesive 150 that has a width that is less than the width of the base 133 (and/or the base 112).

The skin-contact adhesive 150 is generally a pressure-sensitive adhesive, and particularly is a pressure-sensitive adhesive that is capable of securely but releasably adhering or bonding to skin (e.g., mammalian skin). The skin-contact adhesive 150 is also generally safe and non-toxic. Skin-contact adhesive layers will generally be selected according to the desired end use of the apparatus 100. In some embodiments, the apparatus 100 can include more than one skin-contact adhesive 150. Where the apparatus 100 comprises more than one skin-contact adhesive layer 150, each skin-contact adhesive layer 150 may be selected independently of each other with regard to material and thickness used. Examples of suitable adhesives include acrylates, silicones, polyisobutylenes, synthetic rubber, natural rubber, and copolymers and mixtures thereof. Acrylates and silicones can be preferred skin-contact adhesives 150. In general, the skin-contact adhesive 150 should cause little or no irritation or sensitization of the skin during the intended wear period.

In some embodiments, the skin-contact adhesive 150 can be an acrylate (or methacrylate) copolymer. Acrylates will typically have an inherent viscosity greater than about 0.2 dL/g and will comprise one or more polymerized primary monomers and optionally one or more polar comonomers. Primary monomers suitable for use include alkyl acrylates containing 4 to 12 carbon atoms in the alkyl group and alkyl methacrylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. In some embodiments, the alkyl acrylates can include isooctyl acrylate, 2-ethylhexyl acrylate, n-butyl acrylate, and cyclohexyl acrylate. Polar monomers suitable for use can include those having hydroxyl, amide, or carboxylic, sulfonic, or phosphonic acid functionality. Representative examples include acrylamide, methacrylamide, N-vinyl-2-pyrrolidone, 2-hydroxyethylacrylate, 2-hydroxyethylmethacrylate, hydroxypropylacrylate, acrylic acid, methacrylic acid, pyrrolidonyl ethyl acrylate, and alkoxyethyl acrylates, such as 2-carboxyethylacrylate. In some embodiments, the amount by weight of polar monomer will not exceed about 40% of the total weight of all monomers in order to avoid excessive firmness of the final PSA product. Typically, polar monomers can be incorporated to the extent of about 1% to about 20% by weight. In some embodiments, the polar monomer can be acrylamide.

In some embodiments, the acrylate copolymer can comprise the reaction product of primary and polar monomers and additional optional monomers which, when present, are included in the polymerization reaction in quantities that will not render the adhesive composition non-tacky. The optional additional monomers may be added, for example, to improve performance, reduce cost, or for other purposes. Examples of such optional monomers include vinyl esters, such as vinyl acetate, vinyl chloride, vinylidene chloride, styrene, and macromonomers copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference.

Silicone or polysiloxane pressure-sensitive adhesives include pressure-sensitive adhesives which are based on two major components: a polymer, or gum, and a tackifying resin. The polysiloxane adhesive can be prepared by crosslinking the gum, typically a high molecular weight polydiorganosiloxane, with the resin, to produce a three-dimensional silicate structure, via a condensation reaction in an appropriate organic solvent. The ratio of resin to polymer can be adjusted in order to modify the physical properties of polysiloxane adhesives. Use of capped (or amine-compatible) polysiloxanes can, in some embodiments, be preferred so as to increase drug stability and reduce degradation. Further details and examples of silicone pressure-sensitive adhesives which can be useful are described in the U.S. Pat. No. 4,591,622 (Blizzard et al.); U.S. Pat. No. 4,584,355 (Blizzard et al.); U.S. Pat. No. 4,585,836 (Homan et al.); and U.S. Pat. No. 4,655,767 (Woodard et al.). Suitable silicone pressure-sensitive adhesives are commercially available and include the silicone adhesives sold under the trademarks BIO-PSA® by Dow Corning Corporation, Medical Products, Midland, Mich.

Further description of suitable adhesives may be found in U.S. Pat. No. 5,656,286 (Miranda et al.), U.S. Pat. No. 5,223,261 (Nelson et al.), and U.S. Pat. No. 5,380,760 (Wendel et al.), the disclosures of which are incorporated herein by reference. In some embodiments, the thickness of the skin-contact adhesive 150 can be at least about 10 µm, in some embodiments, at least about 20 µm, and in some embodiments, at least about 40 µm. In some embodiments, the thickness of the skin-contact adhesive 150 can be less than about 2 mm (0.07874 inch), in some embodiments, less than about 1 mm (0.03937 inch), and in some embodiments, less than about 150 microns (5906 microinches).

In some embodiments, a medical grade adhesive can be preferred for the skin-contact adhesive 150. Such a medical grade skin-contact adhesive 150 is can have physical properties and characteristics to be capable of maintaining intimate contact with the skin 50 before, during, and after actuation of the apparatus 100. Securing the actuator 104 (or the housing 102) to the skin 50 can aid in keeping the microneedles 108 inserted into the skin 50.

Release Liners

Release liners, which can be used as at least a portion the release liner 152 (in addition to other release liners that are employed, e.g., to cover at least a portion of the base 112), are available from a variety of manufacturers in a wide variety of proprietary formulations. Those skilled in the art will normally test those liners in simulated use conditions against an adhesive of choice to arrive at a product with the desired release characteristics. Liners which can be suitable for use in apparatuses of the present disclosure can be made of kraft papers, polyethylene, polypropylene, polyester or composites of any of these materials. The liner material can be coated with release agents or low adhesion coatings, such as fluorochemicals or silicones. For example, U.S. Pat. No. 4,472,480 (Olson), the disclosure of which is hereby incorporated by reference, describes low surface energy perfluorochemical liners. The liners can be papers, polyolefin films, or polyester films coated with silicone release materials.

Examples of commercially available silicone coated release papers are POLYSLIK® silicone release papers available from Loparex (Willowbrook, Ill.).

Active Agent

As mentioned above, in some embodiments, active ingredients or agents (e.g., drugs) can be delivered via the microneedles 108 (e.g., via solid or hollow microneedles). Any substance that can be formulated in a fluid and delivered via hypodermic injection may be used as the active agent, including any pharmaceutical, nutraceutical, cosmeceutical, diagnostic, and therapeutic agents (collectively referred to herein as "drug" for convenience). The present description envisions that even a gaseous fluid may be utilized.

Examples of drugs that can be incorporated into the apparatuses of the present disclosure are those capable of local or systemic effect when administered to the skin. Some examples include buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as $H_2$ antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-clquinolin-1-yl)butyl] methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatriptan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; antiobesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, interferon-gamma, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, peptide therapeutic agents (natural, synthetic, or recombinant) can be delivered via the microneedles 108 (e.g., via solid or hollow microneedles).

Examples of peptide therapeutic agents that can be incorporated into the apparatuses of the present disclosure include parathyroid hormone (PTH), parathyroid hormone related protein (PTHrP), calcitonin, lysozyme, insulin, insulinotropic analogs, glatiramer acetate, goserelin acetate, somatostatin, octreotide, leuprolide, vasopressin, desmopressin, thymosin alpha-1, atrial natriuretic peptide (ANP), endorphin, vascular endothelial growth factor (VEGF), fibroblast-growth factor (FGF), erythropoietin (EPO), bone morphogenetic proteins (BMPs), epidermal growth factor (EFG), granulocyte colony-stimulating factor (G-CSF), granulocyte macrophage colony stimulating factor (GM-CSF), insulin-like growth factor (IGF), platelet-derived growth factor (PDGF), growth hormone release hormone (GHRH), dornase alfa, tissue plasminogen activator (tPA), urokinase, ANP clearance inhibitors, lutenizing hormone releasing hormone (LHRH), melanocyte stimulating hormones (alpha & beta MSH), pituitary hormones (hGH), adrenocorticotropic hormone (ACTH), human chorionic gonadotropin (hCG), streptokinase, interleukins (e.g. IL-2, IL-4, IL-10, IL-12, IL-15, IL-18), protein C, protein S, angiotensin, angiogenin, endothelins, pentigetide, brain natriuretic peptide (BNP), neuropeptide Y, islet amyloid polypeptide (IAPP), vasoactive intestinal peptide (VIP), hirudin, glucagon, oxytocin, and derivatives of any of the foregoing peptide therapeutic agents.

In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Publication No. 2004/0049150 (Dalton et al.), the disclosure of which is hereby incorporated by reference.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

Microneedles

Microneedle arrays useful for practicing the present disclosure can have a variety of configurations and features, such as those described in the following patents and patent applications, the disclosures of which are incorporated herein by reference. One embodiment for the microneedle arrays includes the structures disclosed in U.S. Patent Application Publication No. 2005/0261631 (Clarke et al.), which describes microneedles having a truncated tapered shape and a controlled aspect ratio. Another embodiment for the microneedle arrays includes the structures disclosed in U.S. Pat. No. 6,091,975 (Daddona et al.), which describes blade-like microprotrusions for piercing the skin. Still another embodiment for the microneedle arrays includes the structures disclosed in U.S. Pat. No. 6,312,612 (Sherman et al.), which describes tapered structures having a hollow central channel Yet still another embodiment for the microneedle arrays includes the structures disclosed in U.S. Pat. No. 6,379,324 (Gartstein et al.), which describes hollow microneedles having at least one longitudinal blade at the top surface of the tip of the microneedle. A further embodiment for the microneedle arrays includes the structures disclosed in U.S. Patent Application Publication Nos. US2012/0123387 (Gonzalez et al.) and US2011/0213335 (Burton et al.), which both describe hollow microneedles. A still further embodiment for the microneedle arrays includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of microneedles that can be employed in the microneedle arrays of the present disclosure are described in PCT Publication No. WO 2012/074576 (Duan et al.), which describes liquid crystalline polymer (LCP) microneedles; and PCT Publication No. WO 2012/122162 (Zhang et al.), which describes a variety of different types and compositions of microneedles that can be employed in the microneedles of the present disclosure. In some embodiments, the microneedle material can be (or include) silicon, glass, or a metal such as stainless steel, titanium, or nickel titanium alloy. In some embodiments, the microneedle material can be (or include) a polymeric material, such as a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Particularly useful types of medical grade polymeric materials include polycarbonate and LCP.

In some embodiments, the microneedle material can be (or include) a biodegradable polymeric material, particularly, a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the microneedles can be a prepared from a dissolvable, degradable, or disintegradable material referred to herein as "dissolvable microneedles". A dissolvable, degradable, or disintegradable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In some embodiments, the microneedles can be made from (or include) a combination of two or more of any of the above mentioned materials. For example, the tip of a microneedle may be a dissolvable material, while the remainder of the microneedle is a medical grade polymeric material.

A microneedle or the plurality of microneedles in a microneedle array useful for practicing the present disclosure can have a variety of shapes that are capable of piercing the stratum corneum. In some embodiments, one or more of the plurality of microneedles can have a square pyramidal shape, triangular pyramidal shape, stepped pyramidal shape, conical shape, microblade shape, or the shape of a hypodermic needle. In some embodiments, one or more of the plurality of microneedles can have a square pyramidal shape. In some embodiments, one or more of the plurality of microneedles can have a triangular pyramidal shape. In some embodiments, one or more of the plurality of microneedles can have a stepped pyramidal shape. In some embodiments, one or more of the plurality of microneedles can have a conical shape. In some embodiments, one or more of the plurality of microneedles can have a microblade shape. In some embodiments, one or more of the plurality of microneedles can have the shape of a hypodermic needle. The shape can be symmetric or asymmetric. The shape can be truncated (for example, the plurality of microneedles can have a truncated pyramid shape or truncated cone shape). In some embodiments, the plurality of microneedles in a microneedle array are solid microneedles (that is, the microneedles are solid throughout). In some embodiments, the plurality of solid microneedles in a solid microneedle array can have a square pyramidal shape, triangular pyramidal shape, stepped pyramidal shape, conical shape, or microblade shape. In a preferred embodiment, the plurality of solid microneedles in a solid microneedle array each have a square pyramidal shape.

In some embodiments, the plurality of microneedles in a microneedle array are hollow microneedles (that is, the microneedles contain a hollow bore through the microneedle). The hollow bore can be from the base of the microneedle to the tip of the microneedle or the bore can be from the base of the microneedle to a position offset from the tip of the microneedle. In some embodiments, one or more of the plurality of hollow microneedles in a hollow microneedle array can have a conical shape, cylindrical shape, square pyramidal shape, triangular pyramidal shape, or the shape of a hypodermic needle.

In some embodiments, one or more of the plurality of hollow microneedles in a hollow microneedle array can have a conical shape. In some embodiments, one or more of the plurality of hollow microneedles in a hollow microneedle array can have a cylindrical shape. In some embodiments, one or more of the plurality of hollow microneedles in a hollow microneedle array can have a square pyramidal shape. In some embodiments, one or more of the plurality of hollow microneedles in a hollow microneedle array can have a triangular pyramidal shape. In some embodiments, one or more of the plurality of hollow microneedles in a hollow microneedle array can have the shape of a hypodermic needle. In a preferred embodiment, the plurality of hollow microneedles in a hollow microneedle array each have the shape of a conventional hypodermic needle.

Figure 12:
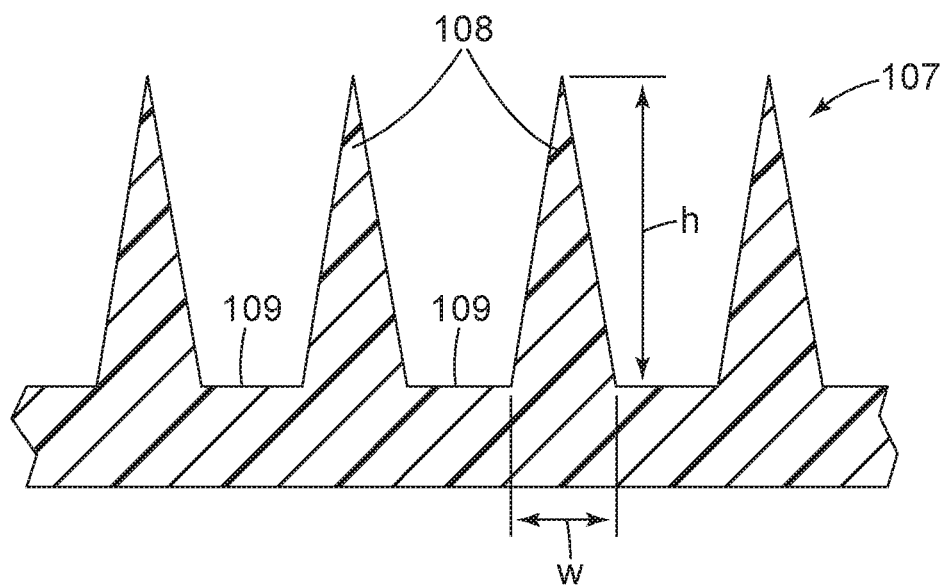
FIG. 12 is a close-up side cross-sectional view of an exemplary microneedle array that can be employed with the apparatus of FIGS. 1-11, the microneedle array shown with the microneedles pointing upwardly.

FIG. 12 shows a portion of the microneedle array 107 that includes four microneedles 108 (of which two are referenced in FIG. 12) positioned on a microneedle substrate 109. Each microneedle 108 has a height h, which is the length from the tip of the microneedle 108 to the microneedle base at substrate 109. Either the height of a single microneedle or the average height of all microneedles on the microneedle array can be referred to as the height of the microneedle, h. In some embodiments, each of the plurality of microneedles (or the average of all of the plurality of microneedles) has a height of about 100 to about 3000 micrometers, in some embodiments, about 100 to about 1500 micrometers, in some embodiments, about 100 to about 1200 micrometers, and, in some embodiments, about 100 to about 1000 micrometers.

In some embodiments, each of the plurality of microneedles (or the average of all of the plurality of microneedles) has a height of about 200 to about 1200 micrometers, about 200 to about 1000 micrometers, about 200 to about 750 micrometers, or about 200 to about 600 micrometers.

In some embodiments, each of the plurality of microneedles (or the average of all of the plurality of microneedles) has a height of about 250 to about 1500 micrometers, about 500 to about 1000 micrometers, or about 500 to about 750 micrometers.

In some embodiments, each of the plurality of microneedles (or the average of all of the plurality of microneedles) has a height of about 800 to about 1400 micrometers.

In some embodiments, each of the plurality of microneedles (or the average of all of the plurality of microneedles) has a height of about 500.

In some embodiments, each of the plurality of microneedles (or the average of all of the plurality of microneedles) has a height of less than about 3000 micrometers. In other embodiments, each of the plurality of microneedles (or the average of all of the plurality of microneedles) has a height of less than about 1500 micrometers. In still other embodiments, each of the plurality of microneedles (or the average of all of the plurality of microneedles) has a height of less than about 1200 micrometers. In yet still other embodiments, each of the plurality of microneedles (or the average of all of the plurality of microneedles) has a height of less than about 1000 micrometers. In further embodiments, each of the plurality of microneedles (or the average of all of the plurality of microneedles) has a height of less than about 750 micrometers. In still further embodiments, each of the plurality of microneedles (or the average of all of the plurality of microneedles) has a height of less than about 600 micrometers.

In some embodiments, each of the plurality of microneedles (or the average of all of the plurality of microneedles) has a height of at least about 100 micrometers. In other embodiments, each of the plurality of microneedles (or the average of all of the plurality of microneedles) has a height of at least about 200 micrometers. In still other embodiments, each of the plurality of microneedles (or the average of all of the plurality of microneedles) has a height of at least about 250 micrometers. In further embodiments, each of the plurality of microneedles (or the average of all of the plurality of microneedles) has a height of at least about 500 micrometers. In still further embodiments, each of the plurality of microneedles (or the average of all of the plurality of microneedles) has a height of at least about 800 micrometers.

In some embodiments employing solid microneedles, each of the plurality of solid microneedles (or the average of all of the plurality of solid microneedles) has a height of about 100 to about 1500 micrometers, about 100 to about 1200 micrometers, about 200 to about 1000 micrometers, about 200 to about 750 micrometers, about 200 to about 600 micrometers, or about 500 micrometers.

In some embodiments employing hollow microneedles, each of the plurality of hollow microneedles (or the average of all of the plurality of hollow microneedles) has a height of about 100 to about 3000 micrometers, about 800 to about 1400 micrometers, or about 500 micrometers.

In some embodiments, each of the plurality of hollow microneedles (or the average of all of the plurality of hollow microneedles) has a height of about 900 to about 1000 micrometers. In other embodiments, each of the plurality of hollow microneedles (or the average of all of the plurality of hollow microneedles) has a height of about 900 to about 950 micrometers. In still other embodiments, each of the plurality of hollow microneedles (or the average of all of the plurality of hollow microneedles) has a height of about 900 micrometers.

A single microneedle or the plurality of microneedles in a microneedle array can also be characterized by their aspect ratio. The aspect ratio of a microneedle is the ratio of the height of the microneedle, h to the width (at the base of the microneedle), w (as shown in FIG. 12). The aspect ratio can be presented as h:w. In some embodiments, each of the plurality of microneedles (or the average of all the plurality of microneedles) has (have) an aspect ratio in the range of 2:1 to 5:1. In some of these embodiments, each of the plurality of microneedles (or the average of all of the plurality of microneedles) has (have) an aspect ratio of at least 3:1.

In some embodiments, the array of microneedles contains about 100 to about 1500 microneedles per cm$^2$ of the array of microneedles.

In some embodiments employing solid microneedles, the array of solid microneedles contains about 100 to about 1500 solid microneedles per cm$^2$ of the array of solid microneedles.

In some embodiments, the array of solid microneedles contains about 200 to about 500 solid microneedles per cm$^2$ of the array of solid microneedles.

In some embodiments, the array of solid microneedles contains about 300 to about 400 solid microneedles per cm$^2$ of the array of solid microneedles.

In some embodiments employing hollow microneedles, the array of hollow microneedles contains about 3 to about 30 hollow microneedles per array of hollow microneedles.

In some embodiments, the array of hollow microneedles contains about 10 to about 30 hollow microneedles per array of hollow microneedles.

In some embodiments, the array of hollow microneedles contains about 3 to about 20 hollow microneedles per array of hollow microneedles.

In some embodiments, the array of hollow microneedles contains about 13 to about 20 hollow microneedles per array of hollow microneedles.

In some embodiments, the array of hollow microneedles contains about 8 to about 18 hollow microneedles per array of hollow microneedles.

In some embodiments, the array of hollow microneedles contains about 18 hollow microneedles per array of hollow microneedles.

In some embodiments, the array of hollow microneedles contains about 12 hollow microneedles per array of hollow microneedles.

In some embodiments, each of the plurality of microneedles (or the average of all of the plurality of microneedles) in a microneedle array can penetrate into the skin to a depth of about 50 to about 1500 micrometers, about 50 to about 400 micrometers, or about 50 to about 250 micrometers.

In some embodiments, each of the plurality of microneedles (or the average of all of the plurality of microneedles) in a microneedle array can penetrate into the skin to a depth of about 100 to about 400 micrometers, or about 100 to about 300 micrometers.

In some embodiments, each of the plurality of microneedles (or the average of all of the plurality of microneedles) in a microneedle array can penetrate into the skin to a depth of about 150 to about 1500 micrometers, or about 800 to about 1500 micrometers.

In some embodiments, each of the plurality of microneedles (or the average of all of the plurality of microneedles) in a microneedle array can penetrate into the skin to a depth of about 400 to about 800 micrometers.

For all of the above embodiments, it will be appreciated that the depth of penetration (DOP) of each of the plurality of microneedles (or the average of all of the plurality of microneedles) in a microneedle array may not be the full length of the microneedles themselves.

In some embodiments, the microneedle array 107 according to the present disclosure can be in the form of a patch, which can include the microneedle array 107, a skin-contact adhesive, such as those described above, and optionally a backing. Whether on a patch or not, the microneedles 108 can be arranged in any desired pattern or arrangement. For example, the microneedles 108 can be arranged in uniformly spaced rows, which can be aligned or offset. In some embodiments, the microneedles 108 can be arranged in a polygonal pattern such as a triangle, square, rectangle, pentagon, hexagon, heptagon, octagon, or trapezoid. In other embodiments, the microneedles 108 can be arranged in a circular or oval pattern.

In some embodiments, the surface area of the substrate 109 covered with microneedles 108, can be about 0.1 cm$^2$ to about 20 cm$^2$. In some of these embodiments, the surface area of the substrate 109 covered with microneedles 108 is about 0.5 cm$^2$ to about 5 cm$^2$. In some other of these embodiments, the surface area of the substrate 109 covered with microneedles 108 is about 1 cm$^2$ to about 3 cm$^2$. In still other of these embodiments, the surface area of the substrate 109 covered with microneedles 108 is about 1 cm$^2$ to about 2 cm$^2$.

In some embodiments, the microneedles 108 of the present disclosure can be disposed over substantially the entire surface of the array 107 (e.g., of the substrate 109). In other embodiments, a portion of the substrate 109 may not be provided with microneedles 108 (that is, a portion of the substrate 109 is non-structured). In some of these embodiments, the non-structured surface has an area of more than about 1 percent and less than about 75 percent of the total area of the device surface that faces the skin surface 50. In another of these embodiments, the non-structured surface has an area of more than about 0.65 cm$^2$ (0.10 square inch) to less than about 6.5 cm$^2$ (1 square inch).

For hollow microneedles, a hollow channel or bore extends through the substrate 109 and microneedles 108. In some embodiments, the bore exits at a channel opening at or near the tip of the hollow microneedle. The channel preferably exits at an opening near the tip of the hollow microneedle. Most preferably, the channel or bore continues along a central axis of the microneedle, but exits similar to a hypodermic needle on a sloping side-wall of the microneedle to help prevent blockage of the channel by tissue upon insertion. In some embodiments, the diameter of the channel bore is about 10 to about 200 micrometers. In other embodiments, the diameter of the channel bore is about 10 to about 150 micrometers. In still other embodiments, the diameter of the channel bore is about 30 to about 60 micrometers.

In some embodiments of hollow microneedles, the average cross-sectional area of the channel bore is about 75 to about 32,000 micrometers. In other embodiments of hollow microneedles, the average cross-sectional area of the channel bore is about 75 to about 18,000 micrometers. In still other embodiments of hollow microneedles, the average cross-sectional area of the channel bore is about 700 to about 3,000 micrometers.

In some embodiments of hollow microneedle arrays, the average spacing between adjacent microneedles (as measured from microneedle tip to microneedle tip) is between about 0.7 mm and about 20 mm. In other embodiments of hollow microneedle arrays, the average spacing between adjacent microneedles is between about 0.7 mm and about 10 mm. In still other embodiments of hollow microneedle arrays, the average spacing between adjacent microneedles is between about 2 mm and about 20 mm. In still other embodiments of hollow microneedle arrays, the average spacing between adjacent microneedles is between about 2 mm and about 10 mm. In a preferred embodiment of hollow microneedle arrays, the average spacing between adjacent microneedles is between about 2 mm.

In some embodiments of hollow microneedle arrays, the average spacing between adjacent microneedles (as measured from microneedle tip to microneedle tip) is greater than about 0.7 mm. In other embodiments of hollow microneedle arrays, the average spacing between adjacent microneedles is greater than about 2 mm.

In some embodiments of hollow microneedle arrays, the average spacing between adjacent microneedles is less than about 20 mm. In other embodiments of hollow microneedle arrays, the average spacing between adjacent microneedles is less than about 10 mm.

In some embodiments of solid microneedle arrays, the average spacing between adjacent microneedles (as measured from microneedle tip to microneedle tip) is between about 200 micrometers and about 2000 micrometers. In other embodiments of solid microneedle arrays, the average spacing between adjacent microneedles is between about 200 micrometers and about 600 micrometers. In still other embodiments of solid microneedle arrays, the average spacing between adjacent microneedles is between about 200 micrometers and about 300 micrometers. In yet still other embodiments of solid microneedle arrays, the average spacing between adjacent microneedles is between about 500 micrometers and about 600 micrometers.

In some embodiments of solid microneedle arrays, the average spacing between adjacent microneedles (as measured from microneedle tip to microneedle tip) is greater than about 200 micrometers. In other embodiments of solid microneedle arrays, the average spacing between adjacent microneedles is greater than about 500 micrometers.

In some embodiments of solid microneedle arrays, the average spacing between adjacent microneedles is less than about 2000 micrometers. In other embodiments of solid microneedle arrays, the average spacing between adjacent microneedles is less than about 1000 micrometers. In still other embodiments of solid microneedle arrays, the average spacing between adjacent microneedles is less than about 600 micrometers. In yet still other embodiments of solid microneedle arrays, the average spacing between adjacent microneedles is less than about 300 micrometers.

The microneedle arrays can be manufactured in any suitable way such as by injection molding, compression molding, metal injection molding, stamping, photolithography, or extrusion. In one embodiment, hollow microneedle arrays can be made by thermocycled injection molding of a polymer such as medical grade polycarbonate or LCP, followed by laser drilling to form the channels of the microneedles.

The following embodiments are intended to be illustrative of the present disclosure and not limiting.

EMBODIMENTS

1. A microneedle injection apparatus comprising:
   a housing having a base and a cavity that extends through the base to define an opening in the base, wherein the base of the housing is configured to be positioned toward a skin surface;
   a microneedle array comprising a first side comprising a plurality of microneedles;
   a microneedle array holder configured to hold a microneedle array and located in the housing, the microneedle array holder movable with respect to the opening in the base of the housing between
      a retracted position in which the microneedle array is recessed within the housing such that the microneedle array does not contact the skin surface when the apparatus is positioned on the skin surface and the microneedle array is coupled to the microneedle array holder, and
      an extended position in which at least a portion of the microneedle array is positioned to contact the skin surface via the opening when the apparatus is positioned on the skin surface and the microneedle array is coupled to the microneedle array holder; and
   a cover configured to be positioned to cover the opening in the base of the housing, the cover including
      a first portion configured to cover at least a portion of the base of the housing adjacent the opening, and
      a second portion configured to be received in the cavity of the housing and further configured to cover the plurality of microneedles on the microneedle array when the microneedle array holder is in the retracted position.

2. The apparatus of embodiment 1, wherein the cover is configured to be coupled to the housing.

3. The apparatus of embodiment 1 or 2, wherein at least a portion of the base of the housing adjacent the opening includes a skin-contact adhesive, and wherein the cover is configured to cover at least the portion of the base including the skin-contact adhesive.

4. The apparatus of any of embodiments 1-3, wherein at least a portion the base of the housing adjacent the opening includes a skin-contact adhesive and further comprising a release liner coupled to the adhesive on the base of the housing, the cover configured to cover at least the portion of the base of the housing including the release liner.

5. The apparatus of any of embodiments 1-4, wherein the first portion and the second portion of the cover are integrally formed.

6. The apparatus of any of embodiments 1-5, wherein the first portion and the second portion of the cover are configured to be coupled together.

7. The apparatus of any of embodiments 1-6, wherein the second portion of the cover is configured to extend through the opening in the base of the housing and into the cavity of the housing.

8. The apparatus of any of embodiments 1-7, wherein the second portion of the cover is tubular in shape.

9. The apparatus of any of embodiments 1-8, wherein the first portion of the cover includes a recess dimensioned to receive at least a portion of the base of the housing.

10. The apparatus of any of embodiments 1-9, wherein the second portion of the cover is centrally located with respect to the first portion of the cover.

11. The apparatus of any of embodiments 1-10, wherein the second portion of the cover includes a recess dimensioned to receive the plurality of microneedles protruding from a first surface on the first side of the microneedle array.

12. The apparatus of embodiment 11, wherein the recess in the second portion of the cover is defined by an inner surface, and wherein the inner surface of the cover and the first side of the microneedle array together define a chamber for housing the plurality of microneedles prior to use.

13. The apparatus of embodiment 12, wherein the chamber is a sterile chamber.

14. The apparatus of any of embodiments 1-13, wherein the second portion of the cover includes a microneedle-facing recess, and wherein the first side of the microneedle array includes a cover-facing recess, and further comprising a sealing member dimensioned to be received in the microneedle-facing recess and the cover-facing recess.

15. The apparatus of embodiment 14, wherein the second portion of the cover includes a sealing member configured to be coupled to at least one of the microneedle array and the microneedle array holder to define a chamber for housing the plurality of microneedles prior to use.

16. The apparatus of any of embodiments 1-15, wherein the first portion of the cover is configured to protect at least the portion of the base of the housing configured to be coupled to the skin surface.

17. The apparatus of any of embodiments 1-16, wherein the second portion of the cover is configured to be coupled to the first side of the microneedle array to enclose the plurality of microneedles.

18. The apparatus of any of embodiments 1-17, wherein the second portion of the cover is configured to be coupled to at least one of the microneedle array and the microneedle array holder.

19. The apparatus of any of embodiments 1-18, wherein the microneedle applicator further includes an actuator movable with respect to the housing between a first position and a second position to cause the microneedle array holder to move from the retracted position to the extended position, wherein, at least when the actuator is in the first position, at least a portion of the actuator protrudes from the opening in the base of the housing and defines a base configured to be coupled to the skin surface, and wherein the cover is configured to cover at least the base of the actuator.

20. The apparatus of embodiment 19, wherein the cover is removable from the remainder of the apparatus, and wherein when the cover is coupled to the apparatus, the cover is positioned to prevent the actuator from being moved to its second position.

21. The apparatus of any of embodiments 1-20, wherein the housing includes a protrusion that defines the base of the housing, and wherein the first portion of the cover includes a recess dimensioned to receive the protrusion of the housing.

22. The apparatus of embodiment 21, wherein the microneedle applicator further includes an actuator movable with respect to the housing between a first position and a second position to cause the microneedle array holder to move from the retracted position to the extended position, wherein, at least when the actuator is in the first position, at least a portion of the actuator protrudes from the opening in the base of the housing and defines a base configured to be coupled to the skin surface, wherein the recess is dimensioned to receive the protrusion of the housing and at least a portion of the actuator, at least when the actuator is in the first position.

23. The apparatus of any of embodiments 1-22, further comprising a sealing member dimensioned to be received in a recess of at least one of the microneedle array and the microneedle array holder that surrounds the plurality of microneedles to define a chamber for housing the plurality of microneedles.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A method of actuating a microneedle injection apparatus, the microneedle injection apparatus comprising:
    a housing having a base and a cavity that extends through the base to define an opening in the base, wherein the base of the housing is configured to be positioned toward a skin surface;
    a microneedle array comprising a first side comprising a plurality of microneedles;
    a microneedle array holder configured to hold a microneedle array and located in the housing, the microneedle array holder movable with respect to the opening in the base of the housing between
        a retracted position in which the microneedle array is recessed within the housing such that the microneedle array does not contact the skin surface when the apparatus is positioned on the skin surface and the microneedle array is coupled to the microneedle array holder, and
        an extended position in which at least a portion of the microneedle array is positioned to contact the skin surface via the opening when the apparatus is positioned on the skin surface and the microneedle array is coupled to the microneedle array holder; a
    a cover configured to be positioned to cover the opening in the base of the housing, the cover including
        a first portion configured to cover at least a portion of the base of the housing adjacent the opening, and
        a second portion configured to be received in the cavity of the housing and further configured to cover the plurality of microneedles on the microneedle array when the microneedle array holder is in the retracted position; and wherein the microneedle applicator further includes an actuator movable with respect to the housing between a first position and a second position to cause the microneedle array holder to move from the retracted position to the extended position, wherein, at least when the actuator is in the first position, at least a portion of the actuator protrudes from the opening in the base of the housing and defines a base configured to be coupled to the skin surface, and wherein the cover is configured to cover at least the base of the actuator, wherein the cover is removable from the remainder of the apparatus, and wherein when the cover is coupled to the apparatus, the cover is positioned to prevent the actuator from being moved to its second position;

the method comprising actuating the actuator to move the actuator from the first position to the second position and to move the microneedle array holder from the retracted position to the extended position.

2. The method of claim 1, wherein the cover is configured to be coupled to the housing.

3. The method of claim 1, wherein at least a portion of the base of the housing adjacent the opening includes a skin-contact adhesive, and wherein the cover is configured to cover at least the portion of the base including the skin-contact adhesive.

4. The method of claim 1, wherein at least a portion the base of the housing adjacent the opening includes a skin-contact adhesive and further comprising a release liner coupled to the skin-contact adhesive on the base of the housing, the cover configured to cover at least the portion of the base of the housing including the release liner.

5. The method of claim 1, wherein the second portion of the cover is configured to extend through the opening in the base of the housing and into the cavity of the housing.

6. The method of claim 1, wherein the first portion of the cover includes a recess dimensioned to receive at least a portion of the base of the housing.

7. The method of claim 1, wherein the second portion of the cover includes a recess dimensioned to receive the plurality of microneedles protruding from a first surface on the first side of the microneedle array.

8. The method of claim 1, wherein the recess in the second portion of the cover is defined by an inner surface, and wherein the inner surface of the cover and the first side of the microneedle array together define a chamber for housing the plurality of microneedles prior to use.

9. The method of claim 8, wherein the chamber is a sterile chamber.

10. The method of claim 1, wherein the second portion of the cover includes a microneedle-facing recess, and wherein the first side of the microneedle array includes a cover-facing recess, and further comprising a sealing member dimensioned to be received in the microneedle-facing recess and the cover-facing recess.

11. The method of claim 10, wherein the sealing member configured to be coupled to at least one of the microneedle array and the microneedle array holder to define a chamber for housing the plurality of microneedles prior to use.

12. The method of claim 1, wherein the first portion of the cover is configured to protect at least the portion of the base of the housing configured to be coupled to the skin surface.

13. The method of claim 1, wherein the second portion of the cover is configured to be coupled to at least one of the microneedle array and the microneedle array holder.

14. The method of claim 1, wherein the housing includes a protrusion that defines the base of the housing, and wherein the first portion of the cover includes a recess dimensioned to receive the protrusion of the housing.

15. The method of claim 1, wherein at least one of the plurality of microneedles comprises an active agent.

16. The method of claim 15, wherein the at least one of the plurality of microneedles comprises a lumen and the active agent is disposed in the lumen.

17. The method of claim 15, wherein the method comprises placing a portion of the apparatus adjacent to the skin prior to actuating the actuator.

18. The method of claim 17, wherein movement of the microneedle array holder from the retracted position to the extended position causes at least one of the plurality of microneedles to pierce the skin.

19. The method of claim 3, wherein a drug reservoir is present with the skin-contact adhesive.

20. The method of claim 4, wherein a drug reservoir is present with the skin-contact adhesive.

* * * * *

UNITED STATES PATENT AND TRADEMARK OFFICE
CERTIFICATE OF CORRECTION

PATENT NO. : 10,391,290 B2  
APPLICATION NO. : 15/866526  
DATED : August 27, 2019  
INVENTOR(S) : Scott Burton et al.

It is certified that error appears in the above-identified patent and that said Letters Patent is hereby corrected as shown below:

In the Specification

Column 10  
Line 50, Delete "DELRINO" and insert -- DELRIN® --, therefor.

Column 23  
Line 58, Delete "POLYSLIK®" and insert -- POLYSILK® --, therefor.

Column 24  
Line 34, Delete "-clquinolin-" and insert -- -c]quinolin- --, therefor.  
Line 44, Delete "exanatide);" and insert -- exenatide); --, therefor.  
Line 46, Delete "carbamazine);" and insert -- carbamazepine); --, therefor.  
Line 52, Delete "metaclopromide," and insert -- metoclopramide, --, therefor.

Column 25  
Line 10, Delete "(EFG)," and insert -- (EGF), --, therefor.  
Line 16, Delete "lutenizing" and insert -- luteinizing --, therefor.  
Line 59, Delete "pamedronate;" and insert -- pamidronate; --, therefor.

Column 26  
Line 11, Delete "channel" and insert -- channel. --, therefor.

In the Claims

Column 34  
Line 49, In Claim 1, after "holder;" delete "a".

Column 35  
Line 17, In Claim 4, after "portion" insert -- of --.

Signed and Sealed this  
Twelfth Day of May, 2020

Andrei Iancu  
*Director of the United States Patent and Trademark Office*